(12) United States Patent
Li et al.

(10) Patent No.: US 11,032,984 B2
(45) Date of Patent: Jun. 15, 2021

(54) GENES AND SNP MARKERS ASSOCIATED WITH LINT PERCENTAGE TRAIT IN COTTON, AND USE THEREOF

(71) Applicant: Institute of Cotton Research of the Chinese Academy of Agricultural Sciences, Henan (CN)

(72) Inventors: Wei Li, Henan (CN); Daigang Yang, Henan (CN); Xiongfeng Ma, Henan (CN); Xiaoyu Pei, Henan (CN); Yangai Liu, Henan (CN); Kunlun He, Henan (CN); Fei Zhang, Henan (CN); Zhongying Ren, Henan (CN); Xiaojian Zhou, Henan (CN); Wensheng Zhang, Henan (CN); Zhenyu Wang, Henan (CN); Chengxiang Song, Henan (CN); Kuan Sun, Henan (CN)

(73) Assignee: Institute of Cotton Research of the Chinese Academy of Agricultural Sciences, Henan (CN)

( * ) Notice: Subject to any disclaimer, the term of this patent is extended or adjusted under 35 U.S.C. 154(b) by 0 days.

(21) Appl. No.: 16/635,287

(22) PCT Filed: Apr. 29, 2019

(86) PCT No.: PCT/CN2019/084940
§ 371 (c)(1),
(2) Date: Jan. 30, 2020

(87) PCT Pub. No.: WO2020/038014
PCT Pub. Date: Feb. 27, 2020

(65) Prior Publication Data
US 2020/0404869 A1    Dec. 31, 2020

(30) Foreign Application Priority Data

Aug. 23, 2018  (CN) .......................... 201810967008.3
Dec. 20, 2018  (CN) .......................... 201811563730.7

(51) Int. Cl.
*A01H 1/04*    (2006.01)
*A01H 6/60*    (2018.01)
*C12Q 1/6895*  (2018.01)

(52) U.S. Cl.
CPC ................ *A01H 1/04* (2013.01); *A01H 6/60* (2018.05); *C12Q 1/6895* (2013.01); *C12Q 2565/125* (2013.01); *C12Q 2565/137* (2013.01); *C12Q 2565/627* (2013.01)

(58) Field of Classification Search
CPC . A01H 1/04; A01H 1/02; A01H 6/604; C12Q 1/686; C12Q 2600/16
See application file for complete search history.

(56) References Cited

FOREIGN PATENT DOCUMENTS

| CN | 107354153 A | * | 11/2017 |
|----|-------------|---|---------|
| CN | 107354153 A |   | 11/2017 |
| CN | 109055593 A |   | 12/2018 |
| CN | 109628630 A |   | 4/2019  |
| WO | 2015052732 A3 | | 6/2015 |

OTHER PUBLICATIONS

Hulse-Kemp, Amanda M., et al. "Development of a 63K SNP array for cotton and high-density mapping of intraspecific and interspecific populations of *Gossypium* spp." G3: Genes, Genomes, Genetics 5.6 (2015): 1187-1209 (Year: 2015).*
International Search Report dated Oct. 17, 2019 for PCT/CN2019/084940.
Su et al.; "Detection of Favorable QTL Alleles and Candidate Genes for Lint Percentage by GWAS in Chinese Upland cotton"; Frontiers in Plant Science; vol. 7; Article 1576; Oct. 2016.

* cited by examiner

*Primary Examiner* — Weihua Fan
(74) *Attorney, Agent, or Firm* — Maxwell L. Minch; Maxwell L Minch Esq. PA

(57) ABSTRACT

The present invention discloses genes and SNP markers significantly associated with lint percentage trait in cotton, and use thereof. The genes significantly associated with the lint percentage trait in cotton are genes Gh_D05G1124, Gh_D05G0313, and GhWAKL3. In the present invention, a CottonSNP63K gene array is used for genotyping, and genome re-sequencing data are analyzed to identify SNP markers significantly associated with the lint percentage trait in cotton. Moreover, the present invention also discloses use of the genes and SNP markers, which are significantly associated with the lint percentage trait in cotton, in cotton germplasm identification, breeding, or genetic diversity analysis.

6 Claims, 10 Drawing Sheets
Specification includes a Sequence Listing.

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
atccgctcta gctccaatgc                                              20

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
cagggaactt tcggatactt gga                                          23

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ccgctctagc tccaatgcaa                                              20

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
tcagggaact ttcggatact tgg                                          23
```

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cgctctagct ccaatgcaac                                               20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cagggaactt tcggatactt gg                                            22

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
tccgctctag ctccaatgc                                                19

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
agggaacttt cggatacttg ga                                            22

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
aatccgctct agctccaatg c                                             21

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
agggaacttt cggatacttg gat                                           23

<210> SEQ ID NO 11
<211> LENGTH: 21
<212> TYPE: DNA
<213> ORGANISM: Artificial Sequence
<220> FEATURE:
<223> OTHER INFORMATION: primer
```

```
<400> SEQUENCE: 11
gctctagctc caatgcaact t                                              21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
agggaacttt cggatacttg g                                              21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tctaatccgc tctagctcca                                                20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gggaactttc ggatacttgg at                                             22

<210> SEQ ID NO 15
<211> LENGTH: 338
<212> TYPE: DNA
<213> ORGANISM: Gossypium spp

<400> SEQUENCE: 15
atccgctcta gctccaatgc aacttgtttc attgtaggtc ttctctttcc attcagattc    60
aagcatcttt tgctagctt agcaactgct acaatttctt cttctgcatt atcattcatt    120
accagtggat caacaatgtt gggtaaggaa ttctccttca ttgagtgtag aaaaaagttt    180
gccaagcttc tcaccacttc ctctgattga catgaagaga tgggttttg tcctgatata    240 agttcaacaa gaacaactcc aaaactataa acatcactct tttctgtaaa ttgacttgat    300
cgaaaatatt caggatccaa gtatccgaaa gttccctg                            338

<210> SEQ ID NO 16
<211> LENGTH: 337
<212> TYPE: DNA
<213> ORGANISM: Gossypium spp

<400> SEQUENCE: 16
ccgctctagc tccaatgcaa cttgtttcat tgtaggtctt ctctttccat tcagattcaa    60
gcatcttttt gctagcttag caactgctac aatttcttct tctgcattat cattcattac    120
cagtggatca acaatgttgg gtaaggaatt ctccttcatt gagtgtagaa aaagtttgc    180 caagcttctc accacttcct ctgattgaca tgaagagatg gttttttgtc ctgatataag    240
ttcaacaaga caactccaa aactataaac atcactcttt tctgtaaatt gacttgatcg    300
aaaatattca ggatccaagt atccgaaagt tccctga                             337
```

<210> SEQ ID NO 17
<211> LENGTH: 335
<212> TYPE: DNA
<213> ORGANISM: Gossypium spp

<400> SEQUENCE: 17

| | | | | | |
|---|---|---|---|---|---|
| cgctctagct | ccaatgcaac | ttgtttcatt | gtaggtcttc | tctttccatt | cagattcaag | 60 |
| catcttttg | ctagcttagc | aactgctaca | atttcttctt | ctgcattatc | attcattacc | 120 |
| agtggatcaa | caatgttggg | taaggaattc | tccttcattg | agtgtagaaa | aaagtttgcc | 180 |
| aagcttctca | ccacttcctc | tgattgacat | gaagagatgg | gttttgtcc | tgatataagt | 240 |
| tcaacaagaa | caactccaaa | actataaaca | tcactctttt | ctgtaaattg | acttgatcga | 300 |
| aaatattcag | gatccaagta | tccgaaagtt | ccctg | | | 335 |

<210> SEQ ID NO 18
<211> LENGTH: 336
<212> TYPE: DNA
<213> ORGANISM: Gossypium spp

<400> SEQUENCE: 18

| | | | | | |
|---|---|---|---|---|---|
| tccgctctag | ctccaatgca | acttgtttca | ttgtaggtct | tctctttcca | ttcagattca | 60 |
| agcatctttt | tgctagctta | gcaactgcta | caatttcttc | ttctgcatta | tcattcatta | 120 |
| ccagtggatc | aacaatgttg | ggtaaggaat | tctccttcat | tgagtgtaga | aaaaagtttg | 180 |
| ccaagcttct | caccacttcc | tctgattgac | atgaagagat | gggttttgt | cctgatataa | 240 |
| gttcaacaag | aacaactcca | aaactataaa | catcactctt | ttctgtaaat | tgacttgatc | 300 |
| gaaaatattc | aggatccaag | tatccgaaag | ttccct | | | 336 |

<210> SEQ ID NO 19
<211> LENGTH: 338
<212> TYPE: DNA
<213> ORGANISM: Gossypium spp

<400> SEQUENCE: 19

| | | | | | |
|---|---|---|---|---|---|
| aatccgctct | agctccaatg | caacttgttt | cattgtaggt | cttctctttc | cattcagatt | 60 |
| caagcatctt | tttgctagct | tagcaactgc | tacaatttct | tcttctgcat | tatcattcat | 120 |
| taccagtgga | tcaacaatgt | tgggtaagga | attctccttc | attgagtgta | gaaaaaagtt | 180 |
| tgccaagctt | ctcaccactt | cctctgattg | acatgaagag | atgggttttt | gtcctgatat | 240 |
| aagttcaaca | agaacaactc | caaaactata | aacatcactc | ttttctgtaa | attgacttga | 300 |
| tcgaaaatat | tcaggatcca | agtatccgaa | agttccct | | | 338 |

<210> SEQ ID NO 20
<211> LENGTH: 333
<212> TYPE: DNA
<213> ORGANISM: Gossypium spp

<400> SEQUENCE: 20

| | | | | | |
|---|---|---|---|---|---|
| gctctagctc | caatgcaact | tgtttcattg | taggtcttct | ctttccattc | agattcaagc | 60 |
| atcttttgc | tagcttagca | actgctacaa | tttcttcttc | tgcattatca | ttcattacca | 120 |
| gtggatcaac | aatgttgggt | aaggaattct | ccttcattga | gtgtagaaaa | agtttgcca | 180 |
| agcttctcac | cacttcctct | gattgacatg | aagagatggg | ttttgtcct | gatataagtt | 240 |
| caacaagaac | aactccaaaa | ctataaacat | cactcttttc | tgtaaattga | cttgatcgaa | 300 |

```
aatattcagg atccaagtat ccgaaagttc cct                                  333
```

<210> SEQ ID NO 21
<211> LENGTH: 340
<212> TYPE: DNA
<213> ORGANISM: Gossypium spp

<400> SEQUENCE: 21

```
tctaatccgc tctagctcca atgcaacttg tttcattgta ggtcttctct ttccattcag     60
attcaagcat cttttttgcta gcttagcaac tgctacaatt tcttcttctg cattatcatt   120
cattaccagt ggatcaacaa tgttgggtaa ggaattctcc ttcattgagt gtagaaaaaa   180
gtttgccaag cttctcacca cttcctctga ttgacatgaa gagatgggtt tttgtcctga   240
tataagttca acaagaacaa ctccaaaact ataaacatca ctcttttctg taaattgact   300
tgatcgaaaa tattcaggat ccaagtatcc gaaagttccc                          340
```

<210> SEQ ID NO 22
<211> LENGTH: 6526
<212> TYPE: DNA
<213> ORGANISM: Gossypium hirsutum L.a
<220> FEATURE:
<221> NAME/KEY: misc_feature
<222> LOCATION: (712)..(712)
<223> OTHER INFORMATION: n is a, c, g, or t

<400> SEQUENCE: 22

```
atgggggtat atctcagcac cccaaaaact gagaagttat cagaagatgg tgaaaatgac     60
aagcttcgat ttggattgtc gtccatgcaa ggatggcgtg catctatgga agatgctgta   120
agttctctct ctaccttctc attgtttgac ttaatatact atctttgaat cattaactaa   180
agccatcgga cttgccttct gttaacgaca atcgtaata tctgcttttc atatatctag    240
tatacgtctc ttaacaaggc attaaataat atctagtctt ggccaatatc ctatgtctag   300
tgtattgaat aaatactaat aactgcttat cttacaccta ttcatgcttt cttgacatgg   360
tattaagaat catataactt ttaagctgag tgttaagatc gcatcatcac aaggcagtga   420
gaaagttcct tagcccttta ctgattctat ttttttgaat atcaaatcag attataaaga   480
tttcaaaagt taatctgcta ctttcttaaa gttatttcac attgattgga atgttgtgag   540
tcatgacaat aaattgacat gtaatttctt aaagttattt catattgatg ctaaggaatc   600
aaattacatg atatccatgc taaagataga catgagactt agctggtaat attagtctga   660
tatctatggc acaagggatt ttttttcttt cttttttttt ttttttttt tngtacttgg    720
tgctggttgg agcgtggggg ttagcaccta tggtacccaa cctcgaggat gagtgtttga   780
tatgggtata tgtccaaaac tggcatgctc tatttttttc taagttttt cacatgtttg    840
gaagatcaca cttcgatatc catgtctaaa tatgtgccaa acacaagtgt caaacatgca   900
tatttggaaa atgaagagtc taggtaacat aggacagaag agtgtcagtt tggactttag   960
aaatatttat cccaggttac acttttctaa aattttccat ttagtcctga taacatagga  1020
aaatgaagag tctaggaaac ataggataca aaaacatgtc cttttaattt gagctgtgct   1080
gaaacctaac gtatttatct caagagataa ttttgcttc ttatgcgtgc acacatgctt   1140
ttttttggaa gtaattgctt gatgcatttc caactatgtt ggaaacctgt tatatctatg   1200
atgtttgagg gatacaggtc cttgttaaaa gcatgtctgc tataataatt gatgattatt  1260
tccattttaa ctacaggcca tttttgtacc tcttgataac tcaatttgcc ttcaatgatg   1320
ccatgaattt gtttttatgg ttttttgcagc atgcagcata tctggatctg gacgactcaa  1380
```

```
catcattttt tggtgtttat gatggtcatg gaggtaagga ttgagctccc ttttttttgt    1440
ttgttccttt aattttatc acatcacttt atttttctt taaaaagttc acaaagttta     1500
gatttcagtg aagttttct tcccttgct ggtgctgttt gtattccttc ttccgaatat     1560
aattttagtt attcctttag caaatcttaa ctgaccagta tgtgtgttgg tcttgcactg    1620
gtaaagctac tagagcaaaa ttatgtcttt aaatactgag gttttatgat attacaagag    1680
accgacctgt tgacacctga gtgtgtttaa tacatatcat tggaggcatt agctttctct    1740
gtttgtatgc gtgtgtccctt ttcttttgg ttttgtgcaa atattattat ataacttttc    1800
cttaactgta ggcgaaaggt gcaaccttgt ttgtttagaa acggttattg taacaacttt    1860
tatgttttca attcataaaa aggagacaaa gagaaagcta aaaacttgga tctaaggatg    1920
tatctcatca aatcttgttt tttcttttct tgttttttgtt tttagcactc tttcggtaca    1980
aaataatatc tgaagataat gttgagttga cagttcagtc ccatatagta tacggtgcct    2040
taattggtgg agctattttc ttttatttga aggtcgtttg tagtgtccag ttgagcccaa    2100
taatcctttt aaaatttgac ttgcactgac actccattaa tgattctgaa tataccatca    2160 cccttgatt accagtagag agcaagctgc attttgggct tgcttttctt gtattatgat    2220
gatattttct attagaaaat gagaaaggga ttggagctgg ttaatcacat tactggatgg    2280
gtaagacctg catgtacagg ccatgcctta gttggcaaaa agttcagctt ccaccacagt    2340
tgggttctta agatgcttct ttgtaattga tagagttaag ggcctagaca ctcaactcat    2400
tcttgagttt ctatgcaatg catgcttatg tctggctgca aagtttcttc ttgatttctc    2460
tgctaaaatt ggatttgaat gctttgaaat attgatgcat cttggagagt ttccgggatg    2520
gagggtacct tcctttctca ggcagctttt gataaactga gattatgttc tgcatagtta    2580
atagtatttg taacatttca tgtttgtaaa cttatagaga aagttttag ttcatataag     2640 ttgtgtaggt aaatattggt ttctgtggaa tgctttaaac aaaaaggttg agctgctcac    2700
aacagaattg ttacttttgc tcttgttccc ttttttctta ttgatgcttt catgattttc    2760 acagcttta tacataaaat tagttgttga tctgattaaa ttctttgtac ctagtcattt     2820
aagcatatta tatgtgggtc catttatctg taggcaaagc agtggctaag ttttgtgcca    2880
agcatcttca tcagcaggtg ctcaagcatg aggcgtattc agctggagat attgggactt    2940
cagtacagaa agcttttctc aggttccttt actggattta tttgtgtatt cttttggtag    3000
caatatacgg aagatatgtc atagctcaac cacaaggcag ctgaaaaatt gcctttgaca    3060
tgtaagtaat atgttctaag tttcctagga atcaggcaat ggaccatgtg cttggagctc    3120
catgatcatt gccactcaaa atttgttaat gccatacatg gttgtttaaa gttttccctt    3180
ttcatctaat gaatccctta tgacactgat gaaattgcat tttgttattt acataaatgt    3240
tactgttttt aatggatagt ttatttatag ctccattctg gcatatgcta gtgccactgc    3300 attttgact gtttaggtca ttgttctcta gcatattttg cttttttcac tcatgaactt     3360
gaaatttaag agtatgatca acttcatttt actggataaa atatgatata gtaaggctgc    3420
ttcttgttaa ttgtttcttc tgctatacat gcattcaact gctatttttt ttatcataca    3480
gaatggatga gatgatgtgt ggacaaagag gatggagaga attagcagtc ctgggagata    3540
aaatggacaa agtttctggt tttgttgaag ggtttgtatg gtctcctaag ggtgatgaag    3600
ccaatgacca ttttgatgat tggcctcctg aggaggtatt tttgtgatag aaaactaaat    3660
ttttgtctta ggtgtatgaa gcaatttcat tttgtatgtt actagacaat gtttcagtaa    3720
```

-continued

```
gatctaagct gcaagacctt aagttttct taagttgccg tgctcattca tgcaaaggag    3780
tccaagtttt caactaaccc attacctgtt ctatagtaat atgctctaga ttttggtttt    3840
aggagtattc ttgcataata aactctttat aaattagttt tgttatttgc ttatttggta   3900
aactggaaaa ttgttatggg aataccacta acagaagctt cgtgtcttgt gaactttata   3960
caaacacttt ttatactatt tttagtgaac ttagacgttt ttaattttac caatcaatac   4020
ttttttaggg aaatgactta attgaaccaa ctctatgaag tatgctaatt ttaattgagg   4080
taggatatag tcaggaattg aacatgatta gttaagttca ctatattgtt tttaggccta   4140
gatcaagaga gggttgttaa caaaggaaga ggaaagttat tagaaacttt tttgagttct   4200
atgagccttt gagaagccta acaacggag agtggatata attaaggaga aggaagatct    4260
ttgcttgagg ttttaagatt tattacaagg aatttgatac aaactggatt ggaataata    4320
taaaggggc atgtggaccc ttcttatgtt aaaaggggtt ggattcttc ttattttgcc     4380
ctatgattct gtagaagaaa attggaaaac atgaaggaaa ctagcattct gtcgataagt   4440
acactctggt tgtatgttta agaattttct gcaggttacc taggactgtc atttactgtg   4500
gttacttgaa gtatcatttg tgtttgagac tttactatga ttcatttaat tctttcaatg   4560
caataccact aagtaagaag cttttgtttg attggtcaaa tatgtctatt acttgtgaga   4620
ttccgatgtt gacttttctg ttggttgcca actagggttc tcactctgat tttcatggac   4680
ctacttctgg atgcacagcc tgtgttgcaa taattcgaaa caagcaacta gttgttgcta   4740
atgctggtga ttcccgttgt gtaatatcta gaaaggggca ggtacaattt tcttttctgc   4800
agaaccctga aaacagaatt tcagaatttt gtttatttcc acagagcctt tccttaaggc   4860
ctctcaaagt tgtgagatga aaggatttac aagttgaatg acaagtagtg cttttgtcgt   4920
aagtaatat tctagcactt ttaagggact gttgttcttg ccctttaac tgcatggaaa     4980
tggttgtaga aagtagcaca tgcttttacc attttcaatt ttattgatga tattagagtg   5040
aaaaacattt gctctaagtg taatagtcac tatatttatt gctgaactag catgtaaagc   5100
atttatcaat gctccacgtt cagattcctt tttcctttta cctctctcct ttggatacac   5160
aatatggttc ctctttaata cggcatagct tagctgctgc atgctttatt tcatagatgt   5220
cactttttac aggcatataa tttgtctaaa gatcacaagc cagaccttga actggagaaa   5280
gataggattc tgaaagctgg tggttttatt caagtcggac gtgtcaatgg aagtttaaac   5340
ttggccaggg ctattggtac cttctagatc caaggggaca atggatctaa tatttatttg   5400
cttgttggtt tatgattgtc tttcacttgc aggagatgcg gagttcaaac agaacaaaac   5460
tttacctgct gaaaggcaaa ttgtaacagc taatccagac atcaacactg taagtgaatt   5520
gctttagcct ttaatatttg tgttatattc tagctctttc agtaaaattt gatgatggtc   5580
aattgattta gtaaagcgac taacttttgt agtattcttt aagcaaaatt aaaaacttct   5640
ttttgtattt tttaaaaaaa tcagacgcat gtataaaact tttgctgcca tttaagcaaa   5700
agatacatcg ttcccaatta gtatccatat ttatccacat gtttataatc tggttttacc   5760
ctctttaaaa taggttgaga tctgcgatga cgatgagttt cttgttttag cttgtgatgg   5820
gatttggtga gtctcctatt gtaagaactt gctttccttt taccctcctg ctctgaaatc   5880
aaccttcagt cctacctgga taccattcag aacacttagg taatttgcag tagatggttc   5940
caggcctgtg acacattctg gatgcacaca tgcctacttg ctaatcattc tcaaagatta   6000
aatatcaagc aatctgtcat aggaaatata tacataacat atatatgctt tgctcatatt   6060
tgtttatgta tgtattatgc attgacatgt gtatatatta atttgctaaa aagataaaga   6120
```

```
gaacgtagtg taccatttat agattccctt gggaattggg agcttgtaag atggccattg    6180
ctgaggattt ttgttttcat taatttgaag atagcattgt tgtgttttgt tgattaggga    6240
ctgtatgtca agtcaacaac tagtggatta tgtacgagag cagttgaatt ctgtaagttc    6300
cttcacaaaa cattataaac ctatcaatat aaagattcca ttaattaact acagatctct    6360
tcccatggtg caggaaacta aactttcagc aatctgtgaa agagtattcg acaggtgctt    6420
ggctccaaca gctggtgggg agggatgcga caacatgaca atgatccttg ttcagttcaa    6480
aaaacctgtt ggttcaggta cttctttgag cagcacccag cattga                  6526
```

<210> SEQ ID NO 23
<211> LENGTH: 3943
<212> TYPE: DNA
<213> ORGANISM: Gossypium hirsutum L.a

<400> SEQUENCE: 23

```
atgtgtttat tagtttcgat ggtgataaca atggagtgtg tcggagctcg gaacttcgcg      60
gcaatggcgg ttcctacacg tgccttttgg aaagcaaatc tgatgaggac taaaacagcg     120
attccaagtc ataatcggct tatttcctta aaggtgagag ctagtggagc aaggagcgag     180
agttgcgttg cggttaaaga agatttcgcc gacgaagaag atttcataaa ggccggtggc     240
tctgagattc tctttgttca aatgcaacaa aataaagaaa tggataaaca gtcgaaatta     300
gcggataagg ttttcacttt gctcacttta gttcgatttt catttgttgg aactaatatc     360
gggagatata tggatatttt cccttttttt ttggttattt ctgcgtgtaa atatggaggc     420
cctactggtg gcttttgagc cacaagaatt tacataaatt ggaaaaaaaa tagttaaata     480
ctcatgaaag ttatgacata tgatggtcac gtgcatctgg tcaatagtat ttggccgcct     540
tctttgccct taattttgt ggtaccacta actagttagc tttgttattt gatgttcgat      600
tggtattttc tattttgat tttatttttt aaaaaattga agaaagattg cattttatta      660 gtgggttta ctgtttcgtt gaaatatcca ttttgagcct ttgtgatagc atatatgttt      720
ttcacagtta ccgcccatat caactgggga aaacgtattg gacctggtag ttattggttg     780
tggtccggct ggtcttgctc ttgctgcaga gtctgctaag ttgggtttaa atgttggact     840
aattggccct gatcttcctt ttaccaataa ttatggagta tgggaagatg agtttaaagg     900
tattcacttc atttctaag caattatgt aagattcatt tcgaagcaat caaataaaca       960
ccaagttaat ctaatgttcg ttttcagatc ttggccttga agatgtatt gagcatgttt      1020 ggcgggacac catagtatac cttgatgatg ataagcctat tatgattggt cgtgcttatg     1080
gacgtgttag tcgatacttg ctccatgagg agttgttgag gaggtaacaa cagctccttg     1140
tcaatgatat ttatggtcat ttttctcttg gttattgctt cttctacttt cccgatcatc     1200
aatgtttaat ttgtattaat tttccctagg tgtatcgagt caggtgtaat gtatcttaac     1260
tcgaaggtag agacgattgt tgaagctacc gatggtcata atcttgtagt tgtgaacac     1320 aatcgtgtcg ttccttgctg gtactataat ttcttttttct cgtactgcta ttcctaaact    1380
tttaaccttt tagtatcaca actccttca agcccctaat gtgctattat aggcttgcta     1440
ctgttgcttc aggagcagct tcaggtaaac tgttgcaata tgaggtaggg ggtccaaggg     1500
tctctgttca aacagcttat ggcgtcgagg ttgaggtacg tatgatacac taactgtgat     1560
tgttaacagt tgtacatatc tttgcatttg ttatttaat ctcactgcag catgaacaga     1620
agattactct ttaagagggc gatggaagaa aaaatttctg aacttattta acaggatacc     1680
```

```
tttttcttat tacatcaggt ggataacaat ccttatgatc caagcctgat ggttttcatg    1740
gattacagag actatgctaa acaagaagtt caatctttag aagcacaata tccaacattt    1800
ctttatgcca tgcccatgtc ttcaacaaga gttttttttg aggtttgcac catgcaatta    1860
atttgtttat tgtttatgtt gtatgccatg attaaatgca aaatgattta gaaagttgca    1920
ttgcaggaaa cttgtttggc ctcaaaagat gccatgcctt ttgatttatt aaagaagaag    1980
ctcatgtcaa ggttagagag catgggaatc cggattttaa aagtttatga agaggtaaac    2040
tgcatggtct aataagatac cagattcatt ccgatataat gtatggatta cttttttatca   2100 ttactcagca ccaaaatagg gctgcatgtc agtcatctcc ttgccatttt ataaattggt    2160
gttgatggtc aaaagatgac tttctccaca agtcattttt ctttactatt cctcattcac    2220
gaacagcccc tcaaatttgt tagtagaaaa tcagagaaaa cagctcgtca caaacaatgc    2280
cacatcaaat tcaggattca cctttctatc atagtagcac ataatttgct atcgacttgg    2340 ttttattca ttattctggt caatgatgga gtgcagagcc caatgctctt aatcctggct     2400
tacttagaat taatgcccat ctatctttgc acttctcaat tagtagtcta tctcatttca    2460
ttcctcacat ttccatgttc caactgcatc atgaagtaac atgtgttgaa tgccaatttt    2520
tattagcaag atgccatgtt tcaatctttt gcaggagtgg tcttacatcc cagttggtgg    2580
ttccttgcca aacacagagc agaagaacct tgcatttggt gctgcagcaa gcatggtgca    2640
tccagctact ggtaggaatt gggttaatag atatttcctt caataattaa gacttaatac    2700
tgccaatcta aaccttctta aacaggttat tcggttgtca gatcattgtc agaggctcca    2760
aattatgctt ctgtaattgc aaatatccta agaaggata attctaatgg cttgcttacc     2820
agtgaaagaa ataatgggaa tatctcaatg caaggtatgc tgtgtgattt atcttctttt    2880
cctctcaact tcacccattt aagggtttgt aaacaagttc ttcatcttaa gcaagccaca    2940
gtaatggaaa tcttttttt tttagtaata aagtcatta acaaatcaaa acaaactaaa      3000
ctgaagctct taacgtattc tggacatcat ttttgagcaa ggagcaacag cttggaatca    3060
gatgctcaga acaatgaact gctccatctt gaacagactc aatctttgcc ataaaatcag    3120
ccactttgtt tgcttatact gcatatgcat tatttgggtt tagtaacatg attaatttct    3180
cttggtaaac gtgatgtcaa ttgtcatcct tggtagttgt tgtctttatg atttgtcatt    3240
tttcttttgc ttggcttgta tgattaattt ctcttcataa acgtgatgtt aattgtgtgc    3300
cgtaatgcta tggcgttttg tataatgtat taacaactta aaattcaacg catggtatca    3360
ccctcttagg atgtgttatt ataatttgat tcagcttggg atactctttg cccacaagaa    3420
aggaaacgcc agaggtcatt ctttctcttt gggctagcac tcatactgca actagatatt    3480
gaaggcattc gaacattctt ccatacattc ttccgtttgc caagtggta tgacttcata     3540 tttaccatct tttggtgttt atttataaag aaagccaaga taactaacct ttccctttcc    3600
acatcaccca atattcagc ttttaaactt gagacagaaa acataactcc atgaataaac     3660
aaacctatca ttaatttttt ttaaaattca tcattataaa agaataatg cttgactagc     3720 atgagttgca tacttaaaat tttactttgt aataactaag gaatatattt attgcaggat    3780
gtggcaagga tttcttggtt ctaatctttc ctctgccgat ctcattctgt ttgccttta    3840 tatgtttgtc atagcaccaa acgatatgag aatgtcccct gtcaggcact taatctcaga    3900
tccaactgga gcaactatga taagaacata tctcacaata tag                      3943
```

<210> SEQ ID NO 24
<211> LENGTH: 20

```
<212> TYPE: DNA
<213> ORGANISM: Artificial Sequence
<220> FEATURE:
<223> OTHER INFORMATION: primer

<400> SEQUENCE: 24
ggattctgaa agctggtggt                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
caatttgcct ttcagcaggt                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tgccttttgg aaagcaaatc                                              20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gcaactctcg ttccttgctc                                              20

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tcaagactga tttgcgtttc ca                                           22

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gcgcaaaggt tggtgtcttc                                              20
```

GENES AND SNP MARKERS ASSOCIATED WITH LINT PERCENTAGE TRAIT IN COTTON, AND USE THEREOF

CROSS-REFERENCE TO RELATED APPLICATIONS

The present disclosure claims priority to Chinese Patent Application No. 201810967008.3, filed with the Chinese Patent Office on Aug. 23, 2018, entitled "SNP Markers for Increasing Lint Percentage in Cotton and Methods for Identification and Breeding of High-yielding Cotton", and Chinese Patent Application No. 201811563730.7, filed with the Chinese Patent Office on Dec. 20, 2018, entitled "Genes and SNP Markers Significantly Associated with Lint Percentage Trait in Cotton, and Use Thereof", which are incorporated herein by reference in their entireties.

TECHNICAL FIELD

The present disclosure relates to the field of molecular biology for lint percentage trait in cotton, and in particular to genes and SNP markers associated with lint percentage trait in cotton, and use thereof.

BACKGROUND ART

Cotton is a major source of natural textile fiber and is also an important cash crop in the world. Upland cotton (*Gossypium hirsutum* L.), which is an allotetraploid cotton variety, accounts for approximately 95% of global cotton yield. Yield is an important economic trait of cotton, and increasing cotton yield has always been an important target for cotton breeding programs, wherein lint yield is an important measure of cotton yield, which consists of the number of plants per unit area, the number of bolls per plant, the weight of single boll, lint percentage, and other factors. Studies have uncovered a significant positive correlation between lint percentage and lint yield. However, in traditional breeding programs, the lint percentage trait is improved only by means of field phenotypic identification, with low efficiency and high false positives. Therefore, the identification of molecular markers and genes closely associated with the lint percentage trait and the targeted improvement of the lint percentage trait by molecular breeding means have important theoretical and practical value for cotton breeding.

The lint percentage trait in cotton is a typical quantitative trait regulated by the minor-polygene. In previous studies, it is the most commonly used strategy to analyze the genetic mechanism of the lint percentage trait in cotton based on biparental hybrid progeny populations. A number of interspecific and intraspecific genetic maps are constructed based on mapping populations for linkage analysis in cotton and are used widely in related studies of complex quantitative traits in cotton. The research of QTL (Quantitative Trait Locus) mapping of cotton yield and fiber quality traits has yielded fruitful results. Currently, researchers have used different mapping populations to identify a total of 4,882 QTLs associated with traits such as cotton yield, fiber quality, stress resistance, and seed. Among them, there are 327 QTL loci associated with the lint percentage trait, which are distributed on different chromosomes. Because of limitations such as the time-consuming construction of mapping populations and the low mapping accuracy of linkage analysis, it is difficult to achieve fine mapping of QTL loci for the lint percentage trait and cloning of key genes. In summary, the research of the genetic basis of the lint percentage trait is relatively limited, and further relevant research is needed.

SUMMARY

An object of the present disclosure includes, for example, providing genes associated with lint percentage trait in cotton, which are obtained by analyzing a large amount of biological information by using molecular biological means and traits using 276 upland cotton accessions, and which provide a good basis for trait improvement in cotton breeding programs.

The object of the present disclosure also includes, for example, providing SNP markers in genes associated with lint percentage trait in cotton, which can be applied to germplasm identification, breeding or genetic diversity analysis, and provide a good basis for the study of cotton traits.

The object of the present disclosure also includes, for example, providing, a product for detecting the SNP marker to facilitate the detection of the SNP marker.

The present disclosure provides a SNP marker associated with lint percentage trait in cotton, wherein the SNP marker is selected from the group consisting of the following SNP markers and combinations thereof:

a SNP marker located in the 10th exon region of gene Gh_D05G1124 and located at base 6498 from a start codon of the gene Gh_D05G1124, which has a G/A nucleotide;

a SNP marker located in the first exon region of gene Gh_D05G0313 and located at base 176 from a start codon of the gene Gh_D05G0313, which has a G/A nucleotide; and a SNP marker located at locus D02_2254167 on gene GhWAKL3.

In other words, the SNP marker is located at base 6498 of a nucleic acid sequence as set forth in SEQ ID NO: 1, located at base 176 of a nucleic acid sequence as set forth in SEQ ID NO: 2, and/or located at 4075 bp on GhWAKL3.

The present disclosure also provides a primer pair, probe, or array for detecting the SNP marker described above.

In one or more embodiments, the primer pair, probe, or array for detecting the SNP marker described above may be designed based on the gene sequence described above.

In one or more embodiments, the primer pair for detecting the SNP marker on the gene Gh_D05G1124 is set forth in SEQ ID NOs: 24-25; and the primer pair for detecting the SNP marker on the gene Gh_D05G0313 is set forth in SEQ ID NOs: 26-27.

In one or more embodiments, the primer pair for detecting the SNP marker located at locus D02_2254167 on GhWAKL3 includes any one of: sequences set forth in SEQ ID NO. 1 and SEQ ID NO. 2; sequences set forth in SEQ ID NO. 3 and SEQ ID NO. 4; sequences set forth in SEQ ID NO. 5 and SEQ ID NO. 6; sequences set forth in SEQ ID NO. 7 and SEQ ID NO. 8; sequences set forth in SEQ ID NO. 9 and SEQ ID NO. 10; sequences set forth in SEQ ID NO. 11 and SEQ ID NO. 12; and sequences set forth in SEQ ID NO. 13 and SEQ ID NO. 14.

The present disclosure also provides a kit comprising the primer pair, probe, or array described in the present disclosure.

The present disclosure also provides use of at least one of the SNP markers described in the present disclosure in cotton germplasm identification, breeding, or genetic diversity analysis.

In one or more embodiments, at least one of the SNP markers is used for the identification and breeding of cotton with high lint percentage.

The present disclosure also provides a method for identifying high-yielding cotton, comprising the steps of: extracting a genome from cotton to be detected; and detecting at least one of the SNP markers described in the present disclosure, wherein the cotton is a high-yielding plant if the SNP marker is a GG genotype.

The present disclosure also provides a cotton breeding method, comprising the steps of: extracting a genome from cotton to be detected; detecting at least one of the SNP markers described in the present disclosure; and selecting a GG genotype as a high-yielding plant for continued crossbreeding.

In one or more embodiments, the cotton to be detected includes materials suitable for sexual propagation, vegetative propagation, or tissue culture of regenerable cells.

In one or more embodiments, the materials suitable for sexual propagation are selected from pollen, ovaries, ovules, embryo sacs, and egg cells.

In one or more embodiments, the materials suitable for vegetative propagation are selected from cuttings, roots, stems, cells, and protoplasts.

In one or more embodiments, the materials suitable for tissue culture of regenerable cells are selected from leaves, pollen, embryos, cotyledons, hypocotyls, meristematic cells, roots, root tips, anthers, flowers, seeds, and stems.

In one or more embodiments, the method of detecting the SNP marker includes one or more of: an agarose gel electrophoresis-based SNP detection method, a DNA sequencing method, a DNA array method, denaturing high-performance liquid chromatography, or mass spectrometry.

The present disclosure also provides a gene significantly associated with lint percentage trait in cotton, which is gene Gh_D05G1124, gene Gh_D05G0313, and/or gene GhWAKL3, wherein the gene Gh_D05G1124 has a nucleic acid sequence as set forth in SEQ ID NO: 22, and the gene Gh_D05G0313 has a nucleic acid sequence as set forth in SEQ ID NO: 23.

In one or more embodiments, the gene significantly associated with lint percentage in cotton is a sequence in the 10th exon region of the gene Gh_D05G1124 and/or a sequence in the first exon region of the gene Gh_D05G0313.

The present disclosure also provides a vector comprising the gene significantly associated with lint percentage in cotton described in the present disclosure or an antisense strand thereof.

The present invention also provides a host comprising the vector described in the present disclosure.

The present disclosure also provides use of at least one of the genes significantly associated with lint percentage trait in cotton described in the present disclosure in the identification and breeding of cotton with high lint percentage.

In one or more embodiments, genes Gh_D05G1124 and Gh_D05G0313 associated with high lint percentage in cotton are screened out in the present disclosure by the following methods. 276 upland cotton accessions are used as materials and planted in multiple environments. A CottonSNP63K gene array is used for genotyping, and a total of 10,660 high-quality SNPs are obtained and used for genetic structure analysis and GWAS. A total of 23 SNPs corresponding to 15 QTLs are found by the GWAS analysis to be significantly associated with the lint percentage trait. In addition, Gh_D05G1124 and Gh_D05G0313 are determined by qRT-PCR analysis as candidate genes for regulating the lint percentage trait. Both the genes Gh_D05G1124 and Gh_D05G0313 are located on chromosome Dt05 of cotton.

It has been found in the present disclosure that the lint percentage trait is mainly associated with nucleic acid changes at SNP loci, SNP markers significantly associated with lint percentage are obtained, and the phenotypic value of the lint percentage trait is positively correlated with the aggregation of favorable allelic variants at the SNP loci. Therefore, the SNP markers significantly associated with lint percentage provide theoretical support for the study and application of the lint percentage trait in cotton.

It is found by further analysis of genes Gh_D05G1124 and Gh_D05G0313 that the sequence in the 10th exon region of the gene Gh_D05G1124 and the sequence in the first exon region of the gene Gh_D05G0313 have significant effects on the lint percentage trait.

In one and more embodiments related to the SNP marker located at locus D02_2254167 on gene GhWAKL3, the sequences set forth in SEQ ID NO. 1 and SEQ ID NO. 2 are amplified to obtain a sequence, it is a favorable variation if the 142th gene is G as set forth in SEQ ID NO. 15, and it is unfavorable if the 142th gene is A. Similarly, the sequences set forth in SEQ ID NO. 3 and SEQ ID NO. 4 are amplified to obtain a sequence, it is a favorable variation if the 140th gene is G as set forth in SEQ ID NO. 16, and it is unfavorable if the 140th gene is A.

Accordingly, the sequences set forth in SEQ ID NO. 5 and SEQ ID NO. 6 are amplified to obtain a sequence as set forth in SEQ ID NO.17, which is a favorable variation; the sequences set forth in SEQ ID NO. 7 and SEQ ID NO. 8 are amplified to obtain a sequence as set forth in SEQ ID NO. 18, which is a favorable variation; the sequences set forth in SEQ ID NO. 9 and SEQ ID NO. 10 are amplified to obtain a sequence as set forth in SEQ ID NO.19, which is a favorable variation; the sequences set forth in SEQ ID NO. 11 and SEQ ID NO. 12 are amplified to obtain a sequence as set forth in SEQ ID NO. 20, which is a favorable variation; and the sequences set forth in SEQ ID NO. 13 and SEQ ID NO. 14 are amplified to obtain a sequence as set forth in SEQ ID NO. 21, which is a favorable variation.

The present disclosure includes at least the following advantageous effects:

(1) A SNP marker associated with lint percentage in cotton is found for the first time in the present disclosure, which can be applied to germplasm identification, breeding or genetic diversity analysis, and provides a good basis for the study of cotton traits.

(2) Accessions with high lint percentage are selected by selecting a favorable allelic variation (GG genotype) at the marker locus, whereby the efficiency and accuracy of the selection are greatly increased, and the number of years required for breeding of accessions with high lint percentage is significantly shortened.

(3) The present disclosure provides genes significantly associated with lint percentage in cotton, which are obtained by analyzing a large amount of biological information using molecular biological means and traits, and which provide a good basis for trait improvement in cotton breeding programs.

(4) The present disclosure provides a product for detecting the SNP marker to facilitate the detection of the SNP marker.

DETAILED DESCRIPTION OF EMBODIMENTS

Embodiments of the present disclosure will be described in detail below in connection with examples, but it will be understood by those skilled in the art that the following examples are only intended to illustrate the present disclosure, and should not be considered as limiting the scope of the present disclosure. Examples are carried out in accordance with conventional conditions or conditions recommended by the manufacturer if no specific conditions are specified in the examples. Reagents or instruments used, whose manufacturers are not specified, are all conventional products that are available commercially.

Example 1

Figure 1:
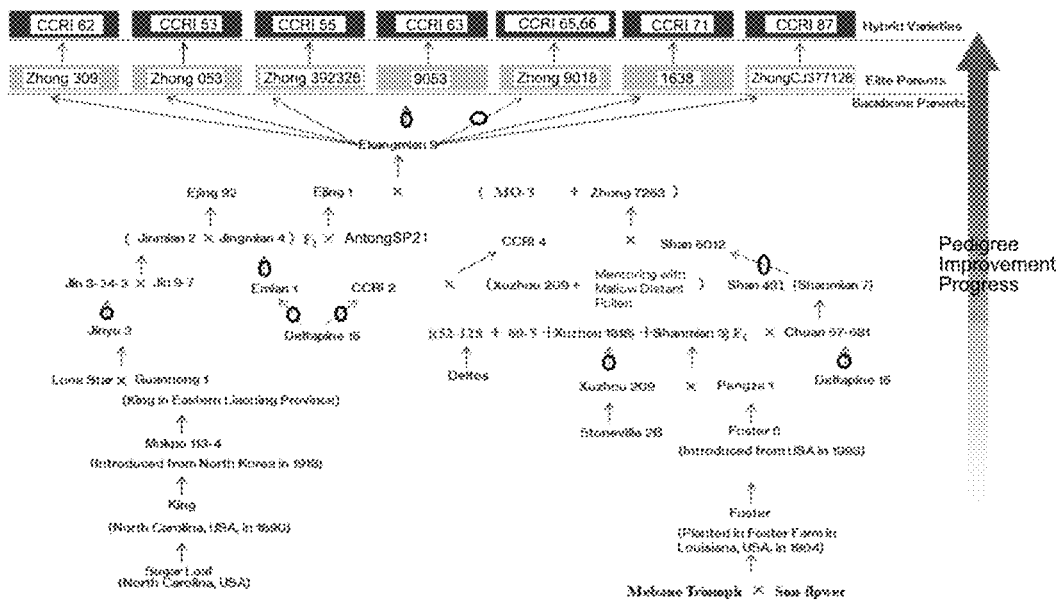
FIG. 1 is a pedigree map showing selective breeding of excellent hybrid parents in Example 1 of the present disclosure, wherein the circled ones are bred by a systematic method, and the others are bred by crossbreeding.

1. Tracking of a Pedigree of Selective Breeding of Female Parents of Hybrid Cotton Exhibiting Strong Heterosis The processes of cultivation and improvement of Ekangmian 9 (a cotton variety) were reviewed, and complete information on pedigree improvement with data available and starting from species introduced from foreign countries was obtained (FIG. 1). During the improvement of the pedigree, genetic components of upland cotton lines King, Deltapine 15, Lone Star, Delfos, Stoneville 2B, and Foster were collected to achieve synchronous improvement of yield, quality, stress resistance, and environmental adaptability.

2. Process of Improvement of Ecological Adaptability in the Yangtze River Basin

It was found, according to our tracking of the breeding process of elite hybrid parents, that the adaptability of these elite varieties in the Yangtze River Basin was mainly inherited from Ejing 1. The earliest origin of Ejing 1 could be traced to Sugar Loaf from North Carolina (NC) in the United States King was bred from the Sugar Loaf by King T. J. in 1890, and introduced into North Korea in 1919, and renamed Mokpo 113-4, and then Guannong 1 was bred after continuous single plant selection for 5 years from 1925 to 1930. This improvement did not significantly increase its yield and quality. It was still of a type with small plant size, small boll and short lint, and it could only be used to weave low-quality yarn, but the special early maturing characteristics of King were retained. Guannong 1 was the first early-maturing variety of upland cotton bred in China. It retained the special early maturing characteristics of Mokpo 113-4, and its adaptability was expanded so that it was more suitable for the northern special-early-maturing cotton area. It had been popularized and planted in Liaoning Province and other places for twenty years since 1933, and then cotton varieties derived from Guannong 1 were labeled with the Liao Cotton series, and up to 166 varieties were derived successively (Brief Introduction to Cotton Germplasm Resources in Liaoning and Utilization Thereof). In the subsequent improvement processes, Guannong 1 was crossed with Lone Star to produce Jinyu 3, which was crossed with Stoneville to produce Jinyu 9. The two varieties played an important role during the selective breeding of early maturing cotton and the whole cotton varieties, and up to 25 and 108 varieties were derived therefrom, respectively (Brief Introduction to Cotton Germplasm Resources in Liaoning and Utilization Thereof). Jin 3-34-3 was derived from Jinyu 3, and Jin 9-7 was derived from Jinyu 9, both of them were early maturing varieties, and their hybrid progeny, Jinmian 2, exhibited as a special early maturing variety.

Deltapine 15 was introduced into China by the Ministry of Agriculture and Forestry of East China in 1950. Deltapine 15 was first popularized in cotton areas in the lower reaches of the Yangtze River and then expanded to cotton areas in the middle reaches of the Yangtze River, and expanded to Sichuan, Guizhou and other places in 1957, and had good adaptability to the ecological characteristics of the Yangtze River Basin. Emian 1 was bred from individuals derived from Deltapine 15 with better natural variations in the Yangtze River Basin by systematic selection, and the adaptability to the ecological characteristics of the Yangtze River Basin was further enhanced. Then, Jingmian 4 was bred from Emian 1 by systematic selection according to the ecological conditions of cotton areas in Jianghan Plain in Hubei Province, which achieved high adaptability to the cotton areas in the Jianghan Plain.

In the 1980s, the Academy of Agricultural Sciences in Jingzhou City, Hubei Province selected a highly heterotic combination of Jinmian 2×Jingmian 4 by hybridization of different ecotypic varieties and by measurement of low-generation combinations. Moreover, high-yielding cotton Ejing 92 was selectively bred from this combination, and was widely popularized in Hubei Province, over a cumulative popularized area of up to 600,000 hm². However, it was a mid-late maturing variety type, and mid-maturing varieties were more suitably popularized in the Yangtze River Basin. Therefore, the Academy of Agricultural Sciences in Jingzhou City selected, from F1 of the highly heterotic combination of Jinmian 2×Jingmian 4, individuals adapted to the ecological characteristics of the Yangtze River Basin, which were further crossed with AntongSP21 to produce Ejing 1. Ejing 1 not only had better yield than Ejing 92, but also was a mid-maturing variety which could be better adapted to the ecological characteristics of the Yangtze River Basin, therefore Ejing 1 was popularized instead of Ejing 92 quickly and became a major variety in the area of Jingzhou City, Hubei Province.

With the increasing requirements for cotton yield, quality and stress resistance during the breeding process, Ejing 1 was further crossed with multiple parents to increase the yield and enhance the stress resistance, and finally Ekangmian 9 was bred. Compared with Ejing 1, Ekangmian 9 was increased in each of the yield, quality and stress resistance, and also maintained the mid-maturation of Ejing 1 and wide adaptability to the Yangtze River Basin, and exhibited excellent traits such as high yield and stable production (strong and uniform production of bolls, high lint percentage), and high quality in the cotton areas in the Yangtze River Basin. Therefore, a number of elite hybrid parents adapted to the ecological characteristics of the Yangtze River Basin could be derived from Ekangmian 9.

3. Process of Improvement of Yield Trait

During the process of improvement of cotton varieties, multiple traits such as adaptability and stress resistance were improved in order to achieve the stabilization or increase of cotton yield and fiber quality in production. Therefore, the process of selective breeding of popularized cotton varieties was always accompanied with yield increase, but different parental accessions had different contribution rates to the yield increase during the breeding process.

Yield was increased by leaps and bounds several times during the selective breeding of pedigree varieties of female parents. During the improvement of Deltapine 15, CCRI (Chinese Cotton Research Institute) 2 and Emian 1, which were selected strains derived from Deltapine 15, were increased in yield by 14.3% and 12.4% compared with Deltapine, respectively. During the improvement of Stoneville 2B, Xuzhou 209 was increased in yield by 15.5% compared with Stoneville 2B acting as a parent and Deltapine 15 acting as a control. Xuzhou 1818, which was a selected strain derived from Xuzhou 209, was further increased in yield by 18.5% compared with Deltapine 15 acting as a control. Moreover, CCRI 4, which was bred from CCRI 2 and Xuzhou 209 by mentoring with Mallow distant pollen, was increased in yield by 12.9% compared with a control variety CCRI 3. Shanmian 7 bred from multiple parents was increased in yield by 17.7% compared with the control variety CCRI 3. During the improvement of Guannong 1, Jinmian 2 was bred with lint percentage being increased by 7%. It could be seen that the improvement of the yield trait of the pedigree mainly resulted from the processes of improvement of Deltapine 15 and Stoneville 2B. Among them, with the successful breeding of CCRI 2, Emian 1, and Xuzhou 209, the yield of pedigree varieties was increased by leaps and bounds.

4. Contribution of Lint Percentage to Yield Increase

Figure 2:
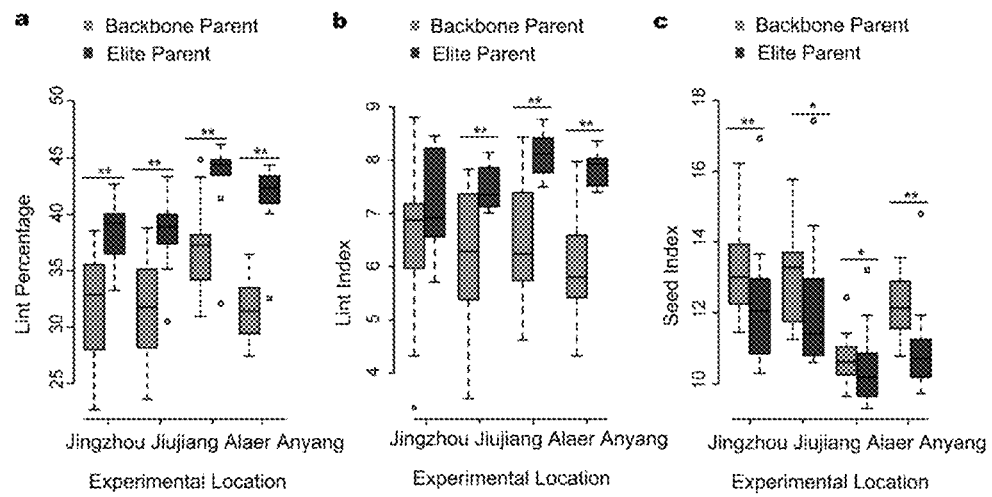
FIG. 2 is a diagram showing differences in lint percentage, lint index, and seed index between backbone parents and elite parents in Example 1 of the present disclosure, where *P<0.05, **P<0.01.

In order to further explore the contribution factor to yield increase during the improvement of the pedigree, 26 pedigree varieties (Table 1) were planted in Anyang, Jingzhou, Jiujiang, and Alaer in 2016, and two replications were set for each experimental location. Field management and trait investigation were carried out in accordance with the Field Management and Field Investigation Record Items in the National Cotton Variety Regional Trials issued by the National Agricultural Technology Extension Service Center. According to the investigation standard, we investigated eight major agronomic traits including lint percentage (LP), lint index (LI) and seed index (SI) as well as fiver fiber quality trait indexes including fiber upper-half mean length (UHML) and fiber uniformity index (UI). It was found by the analysis of data on the major agronomic traits that compared with the nineteen backbone parents, the seven elite parents exhibited an extremely significant increase in lint percentage content in all the four experimental locations (P<0.01) (FIG. 2a), and exhibited an extremely significant increase in lint index in three of the locations (FIG. 2b) (P<0.01). Moreover, it was found by our statistical analysis of data on seed index in the four locations that the elite parents exhibited a significant decrease in seed index content compared with the backbone parents in all the four locations (P<0.05) (FIG. 2c). The experimental results showed that the increase in lint percentage of the elite parents was caused by the increase in lint index and the decrease in seed index. The lint percentage was an important determinant of cotton yield, and the increase in its ratio could facilitate an increase in the yield of the elite parents.

TABLE 1

26 Pedigree Varieties

| No. | Accession Name | Type |
|---|---|---|
| 1 | 9053 | Elite Parent |
| 2 | Zhong 309 | Elite Parent |
| 3 | Zhong 053 | Elite Parent |
| 4 | Zhong 392326 | Elite Parent |
| 5 | Zhong 9018 | Elite Parent |
| 6 | 1638 | Elite Parent |
| 7 | Zhong CJ377126 | Elite Parent |
| 8 | Ekangmian 9 | Backbone Parent |
| 9 | Ejing 1 | Backbone Parent |
| 10 | MO-3 | Backbone Parent |
| 11 | Zhong 7263 | Backbone Parent |

TABLE 1-continued

26 Pedigree Varieties

| No. | Accession Name | Type |
|---|---|---|
| 12 | Jinmian 2 | Backbone Parent |
| 13 | Jingmain 4 | Backbone Parent |
| 14 | AntongSP21 | Backbone Parent |
| 15 | Jin 3-34-3 | Backbone Parent |
| 16 | CCRI 2 | Backbone Parent |
| 17 | Xuzhou 209 | Backbone Parent |
| 18 | Shanmian 7 | Backbone Parent |
| 19 | Jinyu 3 | Backbone Parent |
| 20 | Deltapine 15 | Backbone Parent |
| 21 | Shanmian 3 | Backbone Parent |
| 22 | 52-128 | Backbone Parent |
| 23 | Xuzhou 1818 | Backbone Parent |
| 24 | Chuan 57-681 | Backbone Parent |
| 25 | Guannong 1 | Backbone Parent |
| 26 | Lone Star | Backbone Parent |

Example 2

Genome-wide Re-sequencing of Core Accessions of a Pedigree

1. Genomic DNA Extraction and Quality Detection

Genome-wide DNAs were extracted from 26 test accessions by a modified CTAB method (Paterson et al., 1993), and the purity, integrity and concentration of the samples were detected by agarose gel electrophoresis, a Nanodrop Micro-volume Spectrophotometer, and a Qubit Fluorometer. DNA quality detection results showed that the DNAs of all the samples met the requirements for library construction and sequencing.

2. Library Construction and Computer-Based Sequencing

The Illumina next-generation sequencing reaction was carried out on a Flowcell, and the linkage and fixation of a fragment to be sequenced to the Flowcell were performed by a specific linker, therefore the main purpose of constructing a next-generation sequencing library was to add a linker sequence to the sequence to be sequenced so as to perform sequence determination. Sequence reads in high-throughput sequencing were generally relatively short, and a paired-end sequencing strategy was used in the high-throughput sequencing in order to maximally read a sequence of a genetic fragment while ensuring accuracy and efficiency. Correspondingly, a paired-end library strategy was used in the construction of a next-generation sequencing DNA library.

Library construction and computer-based sequencing were performed by a cooperative company, Novogene Bioinformatics Institute. The main process thereof was as follows: A. Fragment genomic DNA, wherein DNA samples tested to be qualified were randomly broken into fragments with a length of 350 bp by a Covaris crusher; B. End repairing and phosphorylation; C. addition of ployA-tailing; D. addition of a sequencing linker, including Rdl SP, Index, P5, and P7; E. purification, denaturation, and PCR amplification for completing the preparation of the entire library. The library with qualified quality was sequenced using the Illumina HiSeq platform.

A total of 2,357.948 Gb of Raw data was generated in this sequencing and was filtered to obtain 2,350.643 Gb of Clean data, and the samples were sequenced at 30× to obtain Raw data between 73.273 Gb and 110.810 Gb, with sequencing quality Q20>=92.75% and Q30>=85.0%, and with a GC content between 36.78% and 40.01%.

A reference genome had a size of 2,546,077,166 bp, all the samples were aligned at a ratio between 98.92% and 99.71%, and the reference genome (excluding region N) was covered at an average depth of 29.85× to 59.90×, had a coverage at 1× of 94.86% to 98.34% with an average of 97.00%, and had a coverage at 4× between 89.27% and 96.26% with an average of 93.25%.

The sequencing results showed that a sufficient amount of qualified data was produced by the sequencing, which could provide reliable and sufficient raw data for subsequent studies.

Example 3

On the basis of the twenty-six pedigree accessions, deep sequencing data from Stoneville 2B were further collected for analysis (SRR5512449) (Fang et al., 2017). The twenty-seven pedigree accessions were used as a cultivar population, SNP variations in the twenty-seven accessions were detected in accordance with a SNP detection method to obtain the SNP variations of the population. Meanwhile, sequencing data from thirty-one wild cotton varieties were downloaded from a database (Wang et al., 2017). Construction and selective sweep analysis of a phylogenetic tree of the population were performed using the SNP variations detected from the above twenty-seven pedigree varieties and thirty-one wild cotton varieties.

1. Experimental Method 1.1 SNP Detection Method

The detection of SNPs of the test accessions was performed using SAMtools. It mainly comprised the following steps: (1) preparation of a reference genome and its index file, wherein the index of the reference genome was established using a faix command in the SAMtools software; (2) SNP detection, wherein SNPs were detected using a mpileup command in the SAMtools software; (3) extraction of variation loci, wherein perl script was used to extract the variation loci and remove redundant loci; and (4) filtration of the variation loci, wherein loci with an MQ value less than 20 and a depth less than 4 and greater than 1000 were filtered out using vcfutils software.

1.2 SNP Annotation Method

The SNP annotation was performed using ANNOVAR (Wang et al., 2010). The main steps thereof included: (1) data format conversion, wherein the data format conversion was performed using convert2annovar.pl, so that a VCF file outputted by the SNP detection was converted into a format required by the annovar software; (2) database download and construction, wherein a relevant database was downloaded, and might be downloaded using annotate_variation.pl-downdb, or might be downloaded voluntarily and added manually;

(3) SNP Annotation, wherein a database (cotton genome annotation file) was selected as needed, and the SNPs were annotated with protocol parameters in the ANNOVAR program.

1.3 Population Genetic Analysis (1) Data filtering: a minor allele frequency (MAF) and missing value of the population were detected and filtered using VCFtools software (http://vcftools.sourceforge.net), with the filtering standard of MAF=0.05 and Missing=0.2.

(2) Calculation of SNP density: a SNP density in genomes was scanned with a window of 100 Kb and a step size of 20 Kb.

(3) Construction of a neighbor-joining tree: the neighbor-joining tree was constructed using PHYLIP software (Felsenstein J 1989).

(4) Calculation of linkage disequilibrium (LD): the LD was calculated using Plink software, with the parameter "—1d-window-r2 0—1d-window 99999—1d-window-kb 1000" (Purcell et al., 2007).

(5) Calculation of nucleotide diversity (π) the nucleotide diversity π was calculated using VCFtools software (http://vcftools.sourceforge.net), with the main parameter "—window-pi 100000—Window-pi-step 20000".

(6) Selective sweep: the top 5% of ratios of nucleotide diversities between wild cotton and cultivated pedigree cotton ($\pi_{wilds}/\pi_{pedigrees}$) were selected as candidate windows to be selected, and further confirmed by the XP-EHH likelihood method (Sabeti et al., 2007).

2. Experimental Results 2.1 Distribution of a Total Number of SNPs

Figure 3:
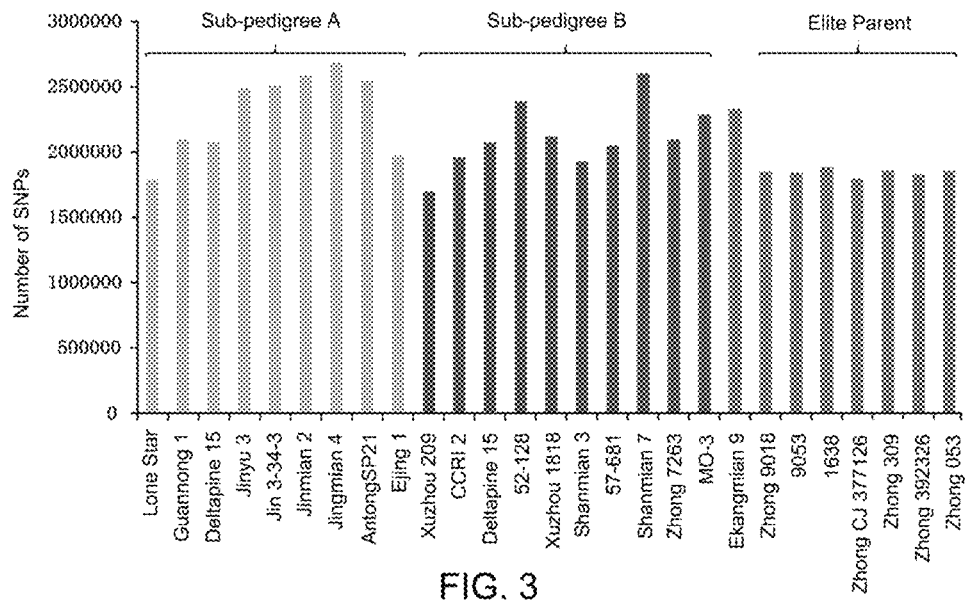
FIG. 3 is a diagram showing the distribution of a total number of SNPs during pedigree improvement in Example 2 of the present disclosure.

A change in the number of SNPs during the variety improvement was shown in FIG. 3.

It was found in the study that the total number of SNPs was not constant during the improvement of pedigree varieties, and experienced a process of increasing first and then decreasing and eventually being stabilized in elite parents. The number of SNPs showed different changes during the improvement of sub-pedigrees A and B, and the number of SNPs increased significantly in the sub-pedigree A (FIG. 3).

The average numbers of SNPs in the earliest four original species in the pedigree, sub-pedigree A, sub-pedigree B, and seven elite parents were 1,915,808, 2,466,682, 2,180,284, and 1,846,299, respectively. During the improvement of sub-pedigree A, the number of SNPs was always maintained at a relatively high level, but was significantly decreased in Ejing 1, thus it could be seen that there were great variations in genome level during the breeding of Ejing 1, and these variations which disappeared during inheritance in the pedigree might be related to a significant increase in yield trait of Ejing 1. The number of SNPs in each accession in sub-pedigree B showed a large fluctuation, but the overall average number was still higher than the original species and elite parents. The seven elite parents had relatively consistent numbers of SNP variations, with a lowest and relatively stable overall average number during the pedigree improvement stage.

2.2 Cluster Analysis of SNP Annotation Results

Figure 4:
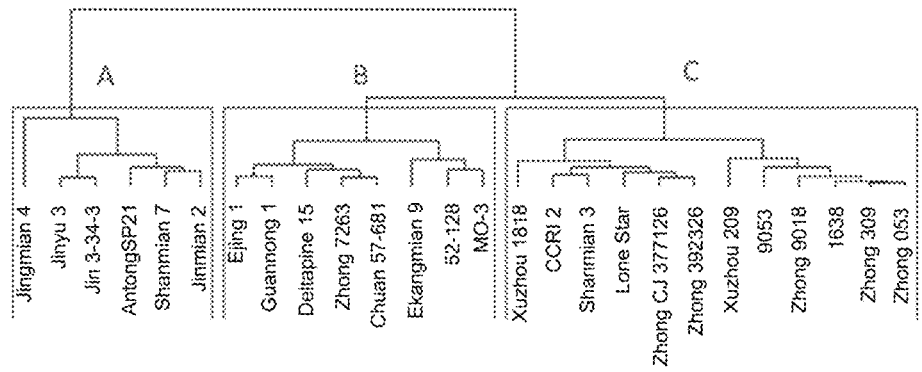
FIG. 4 is a cluster diagram showing SNP annotation results in Example 2 of the present disclosure.

The twenty-six test accessions were divided into three cluster groups A, B and C (FIG. 4).

Group A contained six accessions, five of which were obtained from sub-pedigree A and one of which was obtained from sub-pedigree B, thus it could be seen that the members in cluster group A were mainly obtained from sub-pedigree A. Cluster group B contained eight test accessions, including four accessions obtained from sub-pedigree B, two accessions obtained from sub-pedigree A, Deltapine 15 which was a common accession in the two pedigrees, and Ekangmian 9 which was a core parent. It could be seen that cluster group B was mainly obtained from sub-pedigree B, and it could also be found that Deltapine 15 and Ekangmian 9 were closer to the sub-pedigree B in location and number of SNP variations. There were twelve test accessions in total in cluster group C, including seven elite parents, four accessions in sub-pedigree B, and Lone Star. The inclusion of seven elite parents in cluster group C indicated that the seven elite parents were similar in location and number of SNP variations. This was closely related to the fact that the seven elite parents were derived from the same parent and improved at similar time. The clustering results of the SNP number showed that although there was no strict regularity in variation of the SNP number during the multi-generational improvement of cotton varieties, the differences in SNP number between sub-pedigrees A and B and elite parents could be reflected according to the clustering results.

2.3 Ratio of Non-Synonymous Variations to Synonymous Variations

In this study, it was found, by statistics of the numbers of synonymous variations and non-synonymous variations in exon regions of the twenty-six test accessions, that the numbers of synonymous variations and non-synonymous variations were relatively stable during the improvement of pedigree varieties, the number of synonymous variations was between 28,365 and 35,663 with an average of 30,756, and the number of non-synonymous variations was between 30,896 and 44,108 with an average of 35,091. The ratio of non-synonymous variations to synonymous variations was between 1.09 and 1.24 with an average of 1.14. The results showed that loci with non-synonymous variations were fixed at a higher speed than loci with synonymous variations, which indicated that genes were positively selected in the test accessions. It could be inferred from the results that the favorable variations generated during the artificial breeding of cotton were quickly selected and fixed.

2.4 Distribution of Large-Effect SNPs

In this study, SNP variations that altered a stop codon were referred to as large-effect SNPs, including SNPs causing loss of a stop codon and SNP variations gaining a stop codon. In this study, it was detected that the number of SNP variations gaining a stop codon in the twenty-six test accessions was between 457 and 740, with an average of 552. The number of SNPs causing loss of a stop codon was between 87 and 156, with an average of 107. In each accession, the number of SNP variations gaining a stop codon was greater than the number of SNP variations causing loss of a stop codon. This indicated that a large number of sequences similar to a stop codon sequence were present in the cotton genome and could be converted to a stop codon by a single base variation.

2.5 Distribution of SNP Density in Genome and Zero-Variation Segments

Figure 5:
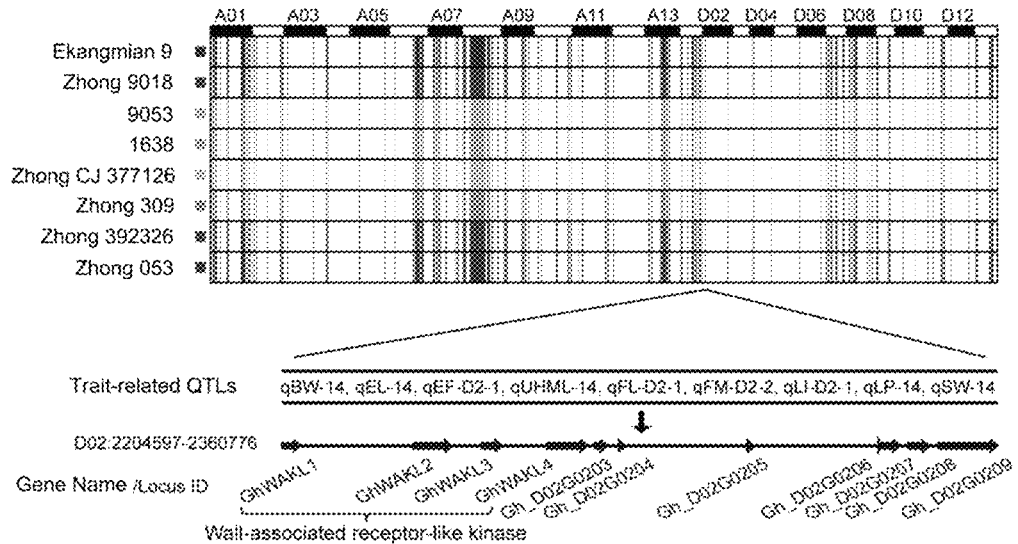
FIG. 5 is a diagram showing common IBDs and key genomic segments of elite parents in Example 3 of the present disclosure.

A genome-wide scanning of the density of SNP variation loci in the twenty-seven pedigree accessions was performed with a window of 100 Kb and a step size of 20 Kb. The genome-wide distribution of chromosomes was shown in FIG. 5. The scanning results showed that the SNP density in the window was between 0 and 0.01303, with an average density of 0.000907 in the whole genome. Statistics of zero-variation windows on the genome were further made. After windows with intersections were combined, a total of 647 segments with zero-variation loci were discovered, the shortest segment was 100 Kb, and the longest segment was 57,500 Kb. The total length on subgenome A was 69,960 Kb, and the total length on subgenome D was 15,840 Kb. The zero-variation segment located on the subgenome A was much larger than that on the subgenome D, and this result suggested that the subgenome A experienced more artificial selections during the pedigree improvement process. There was a highly conserved large segment in chromosome A12, which was located between 29,980,001 bp to 87,480,000 bp and comprised 65.73% of the full length of chromosome A12, and which had no SNP variation locus in the pedigree accessions.

Scanning statistics of the number of SNPs was performed with a window of 1 Mb, the patterns of variation and distribution of the SNP density in the pedigree accessions were detected, and the genetic variation pattern of the SNP density in the pedigree was analyzed in connection with the genetic relationship of the pedigree. First, we detected the SNP density in chromosomes of seven elite parents and explored their distribution patterns. Then, the pedigree accessions were divided in accordance with single-route inheritance by using Ekangmian 9 as a node, and a total of nine genetic routes were established to analyze the genetic variation pattern of the SNP density distribution in the pedigree. It was found by tracking the distribution forms of SNPs in the seven elite parents that the SNP density in the accessions had a certain distribution pattern on the chromosomes, and it was found, by further detection of the SNP density distribution patterns in Ekangmian 9 which was a common parent of the seven elite parents and in three parents of Ekangmian 9, that the distribution of the SNP density on chromosome A01 had a certain genetic pattern in the accessions.

By scanning with a 1 Mb window, chromosome A01 was divided into a total of 99 windows. It was found, by variance analysis of the scanning results of the number of SNP variations on the chromosomes of the seven elite parents, Ekangmian 9, Ejing 1, MO-3 and Zhong 7263, that there were significant differences in the number of SNP variations in different windows (P=0.0001). Further, eight windows with high density of SNPs were obtained by Duncan test, which were windows 21, 41, 79, and 83-87, respectively, wherein windows 83-87 were five consecutively distributed windows.

High-frequency variation regions on the windows 21, 41, 79, and 83-87 were named as high-frequency variation regions $\hat{1}$, $\hat{2}$, $\hat{3}$ and $\hat{4}$, respectively. Among the four high-frequency variation regions, the high-frequency variation region $\hat{1}$ was shared by the seven elite parents, and the other high-frequency variation regions existed in samples 1, 3, 4, 5, 6, and 7 and did not exist in sample 2. We found by the detection of Ekangmian 9 which was the common parent of the seven elite parents that such four high-density variation windows also existed in Ekangmian 9, except that the position of the end of region $\hat{4}$ on the chromosome was shifted forward, and appeared on the window 84. The three parents of Ekangmian 9 were further detected, whereby it was found that the distributions of SNP density in the two male parents, Zhong 7263 and MO-3 showed the same trend but were slightly different in region $\hat{4}$, Zhong 7263 in which the end of region $\hat{4}$ was also shifted forward was kept consistent with Ekangmian 9, but MO-3 was kept consistent with six elite parents. The trend of distribution of SNPs in Ejing 1, which was a female parent of Ekangmian 9, was kept consistent with that of the elite parent 9053. Thus, it could be seen that the SNP density distribution pattern was transmitted with a certain pattern in the pedigree.

In order to explore the genetic pattern of the SNP density distribution on chromosome A01 in detail, regions with high-frequency SNP variations in the accessions were tracked and sorted out in accordance with nine single-route genetic routes.

Scanning statistics of the numbers of SNPs on other chromosomes were made in accordance with the same method, whereby it was found that the chromosomes had high-frequency variation regions similar to those on chromosome A01, except for D06 on which there was no significant high-frequency variation region.

By detecting and sorting out the SNP density distribution in the pedigree, we summarized the following patterns: (1) these high-frequency variation regions were generated during the artificial selective breeding; (2) these high-frequency variation regions might be generated by crossbreeding (Guannong 1×Lone Star→Jinyu 3), or might be generated by selective breeding using a systematic method (Deltapine 15→Jingmian 4, Deltapine 15→Chuan 57-681, Deltapine 15→CCRI 2); (3) these high-frequency variation regions did not disappear and were fixed in the varieties after multi-generation artificial selection.

2.6 Analysis of Population Evolution and Analysis of Linkage Disequilibrium

A phylogenetic tree was constructed using 4 million SNP variations detected by re-sequencing of 31 wild cotton varieties and 27 pedigree accessions. It was indicated that unique genomic variations occurred in the pedigree cultivars under the effect of artificial selection. The nucleotide diversity ($\pi$) of the cultivated pedigree cotton was further calculated to be about $0.36 \times 10^{-3}$, which was less than $1.32 \times 10^{-3}$ calculated according to wild cotton, and also less than $0.67 \times 10^{-3}$ calculated for Chinese cultivated cotton. This result showed that the genomic diversity of the pedigree accessions was reduced compared to both wild cotton and Chinese cultivated cotton, which indicated that the genomic diversity of the cultivars was reduced by artificial directional improvement.

The linkage disequilibrium intensities in the cultivated cotton and wild cotton were estimated. The results showed that the intensity of linkage between pedigree accessions was greater than that of wild cotton, which indicated that the degree of linkage of chromosomes in the pedigree accessions was greatly increased in the case of artificial selection, which suggested that a large number of stably inheritable and fixable haplotypes were formed. Cultivated cotton and wild cotton were different not only in the degree of linkage, but also in the degree of linkage between subgenomes A and D. In the pedigree accessions, the intensity of linkage of subgenome A was higher than that of subgenome D, and there was a relatively great difference between the two subgenomes. In wild cotton, the subgenomes A and D had a consistent trend of decline within a short distance, and the subgenome A was slightly higher than the subgenome D at later stage. This indicated that the intensity of genomic linkage in the pedigree accessions was increased during the experience of artificial improvement.

2.7 Analysis of Selective Sweeps

An identification of selected regions was performed using the nucleotide diversity of wild cotton and cultivated cotton, and the selected regions during the domestication from wild cotton to cultivated cotton were identified by the ratio of $\pi_{wild}/\pi_{cultivar}$. The $\pi$ values of the genomes were calculated with a window of 100 Kb and a step size of 20 Kb, and then the top 5% maximum values of $\pi_{wild}/\pi_{cultivar}$ were taken as selected sections. A total of 4,643 windows were obtained, wherein 2,499 windows were located in the subgenome D, and 2,144 windows were located in the subgenome A. This result further verified the above results of LD calculations, that is to say, the subgenome D was subjected to more artificial selections during the pedigree improvement. After combining adjacent windows, we obtained 1,038 candidate selective sweeps, each segment having a length between 100 Kb and 680 Kb with an average of 155 Kb. These candidate sections were further confirmed by calculating XP-EHH values with the same window size. These sections were re-screened based on the top 5% of the XP-EHH values. Finally, 511 selective sweep sections were obtained, each having a length between 100 Kb and 500 Kb, with a total length of 72.54 Mb. These segments affected a total of 1581 genes, of which 754 genes were in the subgenome A and 827 genes were in the subgenome D. These genes were involved in 103 KEGG pathways and 2,031 GO terms. In addition, there were overlapping regions between these segments and 79 important QTL sections, whereby the importance of these regions to cotton improvement could be reflected.

Example 4

Analysis of Homologous Genetic Materials of Backbone Parents

1. Method for Detecting Homologous Genetic Materials

A method for detecting IBD (identity by descent) (Fang et al., 2017) was used in this test. The detailed steps were as follows:

(1) Genome-wide scanning was performed using a window containing 200 polymorphic SNP loci between parents (the number of SNP loci might be greater than 200, because the same loci between the parents were also located within the window) and using 20 polymorphic SNP loci between parents as a step size to calculate the proportion of polymorphic loci within the window. The inherently conserved segments (Genetic distance≤0.01) in the original species of the pedigree were filtered out according to the statistical results.

(2) SNP consistency between parents and offspring was calculated using 200 SNP loci different between parents as a window and using 20 SNP loci as a step size. A window with a consistency greater than 0.99 in the result was an IBD fragment.

2. Detection Results and Analysis of Homologous Genetic Materials

Zhong 7263, Ejing 1, and MO-3 were the male and female parents of Ekangmian 9 According to the pedigree relationship, we detected and tracked homologous genetic fragments in the pedigree using Zhong 7263, Ejing 1, and Ekangmian 9 as nodes.

Upon detection and analysis, a total of 1,284 unique IBD segments were obtained in the sub-pedigree A, which had a total length of 203.14 Mb, accounting for 10.5% of the genome. Statistics were made on the number and length of IBDs on chromosomes and the proportion of IBDs in the genome. According to the statistical results, we found that 10.5% of the chromosomal genetic components of Ejing 1 could be clearly traced to the genetic sources, of which 5.09% were derived from Jinmian 2, 0.52% were derived from Jingmian 4, and 2.08% were derived from AntongSP21. Here, 0.74% were cumulatively inherited from the original species, Guannong 1, Lone Star, and Deltapine 15.

The patterns of transmission of genomes of the backbone parents were analyzed by the method of detecting homologous genetic fragments, and homologous genetic fragments of 203.14 Mb, 327.40 Mb and 565.71 Mb were obtained in Ejing 1, Zhong 7263, and Ekangmian 9, respectively. These fragments were originated from different backbone parents, could be transmitted from generation to generation during pedigree improvement, and were finally collected into Ejing 1, Zhong 7263, and Ekangmian 9 These fragments overlapped with a large number of QTL sections already located on cotton and had important biological significance.

Example 5

Analysis of Genetic Components of Elite Parents and Acquisition of Key Genomic Segments 1. Experimental Method 1.1 Analysis of Gene Expression Amount (1) Sampling period: fiber materials at −1, 0, 1, 3, 5, 7, 10, 15, and 20 DPA (Day post-anthesis, DPA) were taken for RNA extraction using TM-1 as an experimental material.

(2) RNA extraction: RNAs were extracted using a Biotech RNA extraction kit.

(3) Real-time fluorescent quantitative PCR: primers were designed with GhWAKL1, GhWAKL2, GhWAKL3, and GhWAKL4 as target gene sequences, respectively, and GhHIS3 was used as an internal reference gene for qRT-PCR.

1.2 Principal component analysis (PCA) and kinship analysis (Kinship) were performed using TASSEL 5.0 to obtain matrices of principal components and kinship coefficients. A PCA+K model was selected for association analysis using TASSEL 5.0.

2. Analysis 2.1 Acquisition of Core Homologous Genetic Fragments

Common IBD fragments were extracted from IBDs of the seven elite parents inherited from Ekangmian 9, and a total of 526 common IBD fragments were obtained, each having a length between 12,522 bp and 1,836,814 bp, with a total length of 104,473,421 bp. Their distributions on chromosomes were shown in FIG. 5. It was found from the results that the IBD fragments common to the seven elite parents and inherited from Ekangmian 9 were distributed on the chromosomes non-randomly, and the number of IBDs in the subgenome A was significantly more than that in the subgenome D, and the IBDs were also unevenly distributed within the subgenome, and the largest number of IBDs were distributed on chromosome A08. These common IBD fragments were fragments that could be inherited stably during the improvement of Ekangmian 9, and had important effects on the improvement of yield and quality at the later stage. These common IBD segments contained 1,937 genes, of which 1,173 genes were located in the subgenome A and 764 genes were located in the subgenome D. These genes were involved in 103 KEGG pathways and 2,325 GO terms. These common IBDs contained 26 GWAS loci and 28 QTL loci associated with boll weight, boll number, lint percentage, fiber quality, and the like. In the above IBDs intersecting with QTL loci, the fragment D02: 2204597-2360776 contained nine quantitative trait loci associated with boll weight, lint percentage, seed index, and the like, and also intersected with a GWAS section for lint percentage (P=5.63E−07). This segment contained a total of eleven genes, four of which (Gh_D02G0199, Gh_D02G0200, Gh_D02G0201, Gh_D02G0202) were involved in cell wall development. These four genes were homologous to a cell wall-associated kinase family protein gene (locus ID: ATI G69730) in Arabidopsis, and therefore were named GhWAKL1, GhWAKL2, GhWAKL3, and GhWAKL4, respectively. It was found by further tracking that this fragment might be completely originated from Ejing 1, or might be inherited from Zhong 7263. The fragment in Zhong 7263 could be partially traced back to Xuzhou 209 and 52-128.

2.2 Analysis of Expression Levels of Candidate Genes

Figure 6:
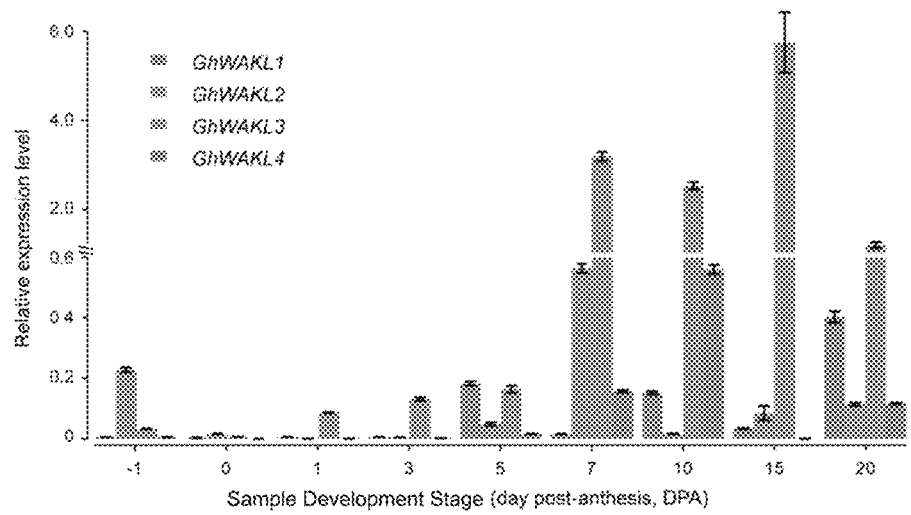
FIG. 6 is a diagram showing the analysis of expression levels of candidate genes in Example 5 of the present disclosure.

The development of cotton fiber was closely related to the morphogenesis of cell wall. In order to further explore the relationship between four candidate genes associated with cell wall kinase and the development of cotton fiber, we detected their expression amounts in different stages of fiber development using real-time fluorescent quantitative PCR technology. The results showed that the expression amounts of these four genes was significantly up-regulated in the later stage of fiber development, and these four genes were highly expressed especially during secondary wall thickening. Compared with the other three genes, GhWAKL3 was expressed in the highest amount (FIG. 6).

Figure 7:
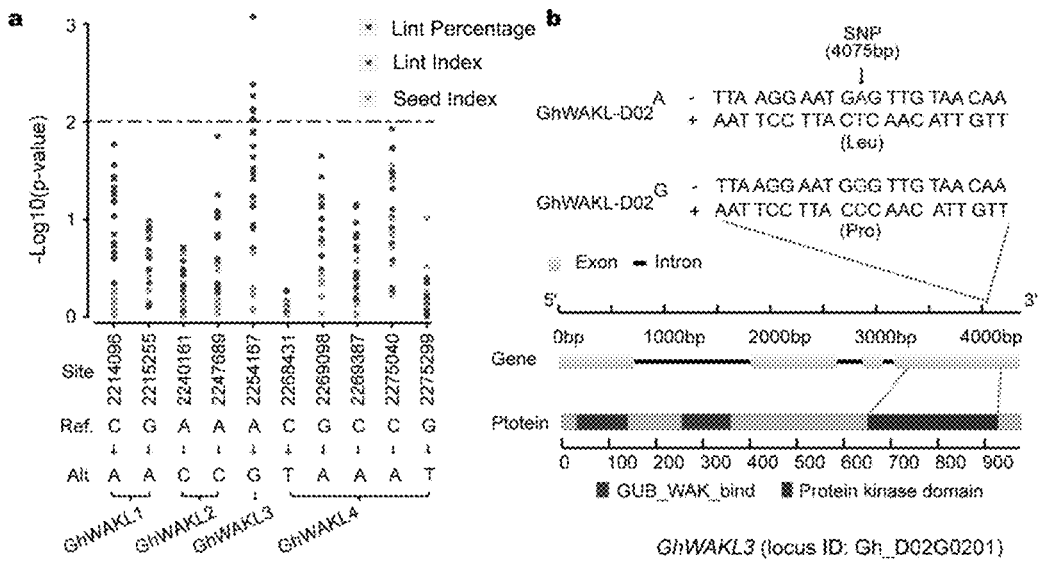
FIG. 7 is a diagram showing association analysis of candidate genes and the structure of a target gene in Example 5 of the present disclosure, where (a) shows analysis of association between GhWAKLs and lint percentage, lint index and seed index, and (b) shows the genetic structure and non-synonymous variation locus of GhWAKL3.

2.3 Analysis of Association between Candidate Genes and Lint Percentage Trait It was found by annotation of the variation detection results that there were ten non-synonymous variation loci on the four candidate genes, wherein GhWAKL1 had two, GhWAKL2 had two, GhWAKL3 had one, and GhWAKL4 had five. Association analysis was performed using a PCA+K model using these non-synonymous variation loci in combination with their genotyping results in 258 cotton varieties as well as phenotypic data on lint percentage, lint index and seed index in multiple locations for multiple years (Fang et al., 2017). The results showed that the locus SNP_D02_2254167 was extremely significantly associated with lint percentage and lint index in multiple environments (P<0.01) (FIG. 7a). This result further clearly showed that GhWAKL3 had an important effect on lint percentage in cotton fiber, similarly to the results of real-time fluorescent quantitative experiments. There were four exon segments on GhWAKL3, and a protein encoded thereby had three conserved domains, two repetitive Wall-associated Receptor Kinase Galacturonan-binding (GUB_WAK_bin), and one protein kinase domain. The variation of the locus SNP_D02_2254167 occurred at 4075 bp on GhWAKL3, at which adenine base were converted to guanine base (A→G), resulting in a change from leucine (Leu) to proline (Pro), which change occurred on the protein kinase domain (FIG. 7b).

Figure 8:
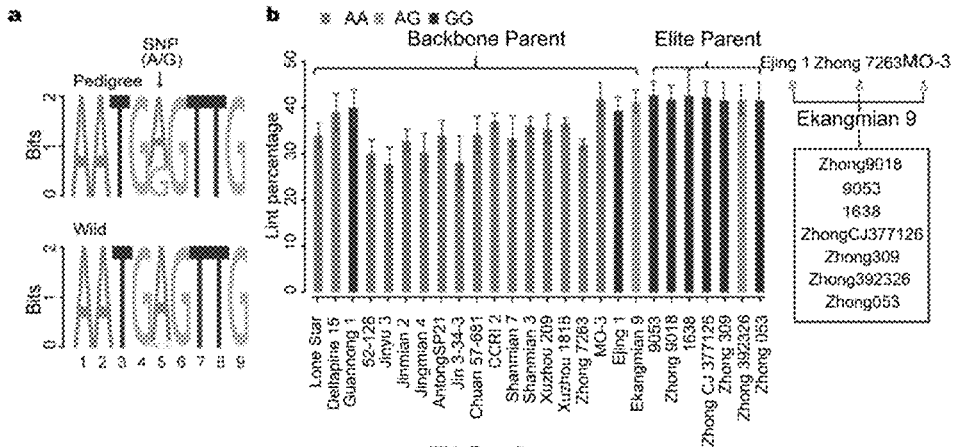
FIG. 8 is a diagram showing genotypic frequencies of candidate loci and their distribution in the pedigree in Example 5 of the present disclosure, where (a) shows comparison of allele frequencies of non-synonymous variation loci of GhWAKL3 in wild cotton and pedigree accessions, and (b) shows genotypic distribution of GhWAKL3 in the pedigree accessions and the corresponding lint percentage trait performance.

The variations of the locus SNP_D02_2254167 on GhWAKL3 had two allelic variants (A/G) in a population. In wild cotton, the frequencies of genes with A and G allelic variants were approximately 93.5% and 6.5%, respectively. In the pedigree, the frequencies of genes with A and G allelic variants were approximately 70.4% and 29.6%, respectively, and the frequency of genes with G allelic variant was increased significantly (FIG. 8a). Moreover, in the pedigree population, the G allelic variants were concentrated in the elite parents, six of the elite parents were of the G allelotype, and only one elite parent was of the A allelotype (FIG. 8b). It could be seen that the artificial selection was directed to retaining the G allelotype.

Figure 9:
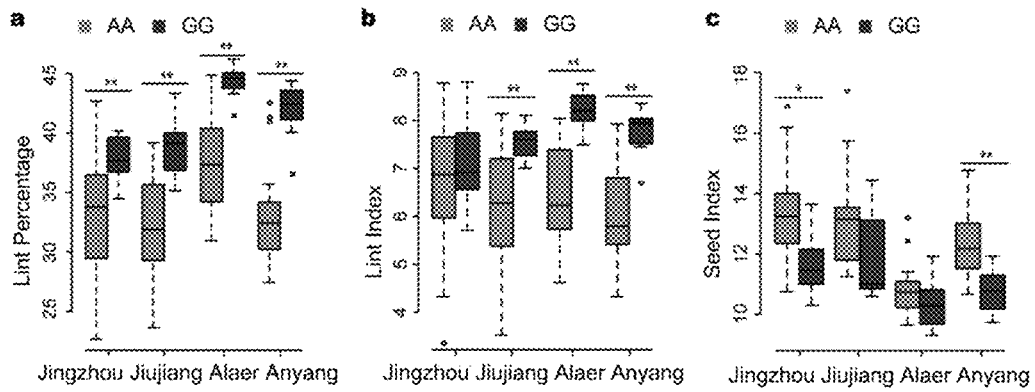
FIG. 9 is a diagram showing the performance of lint percentage, lint index and seed index of different genotypes in Example 5 of the present disclosure, where (a) shows the lint percentage trait performance of different genotypes of GhWAKL3, (b) shows the lint index trait performance of different genotypes of GhWAKL3, and (c) shows the seed index trait performance of different genotypes of GhWAKL3.

The pedigree accessions were classified depending on different A/G allelotypes, and statistics of their field performances in lint percentage, lint index, and seed index were made. It was found from the results that the lint percentage showed an extremely significant difference in all the four planting locations (FIG. 9a); the lint index showed an extremely significant difference in three locations (FIG. 9b); and the seed index reached a significant level of difference in one location and reached a significant difference in one location (FIG. 9c). In order to further confirm the difference between the A and G allelic variations, statistics of the differences in lint percentage, lint index and seed index of 258 cotton germplasms in nine environments were made in accordance with the same method, and the results showed that the lint percentage content reached an extremely significant difference level in all the nine environments; the lint index reached an extremely significant level in five environments, and reached a significant level in three environments; and the difference in seed index reached a significant level in only one environment. Thus, it could be concluded that the allelotype GG was a favorable allelic variation contributing to an increase in lint percentage.

In summary, as can be seen from the calculation results, 10.2% to 33.8% of the genetic components of the seven elite parents were clearly derived from Ekangmian 9 Among them, the proportion of genomes inherited from Ekangmian 9 reached 30% on average in Zhong 9018, 9053, 1638, Zhong 309 and Zhong 053. We extracted common IBD fragments from IBDs of the seven elite parents inherited from Ekangmian 9, whereby a total of 526 common IBD fragments were obtained, each having a length between 12,522 bp and 1,836,814 bp, with a total length of 104,473,421 bp. These common IBDs contained 26 GWAS loci and 28 QTL loci associated with boll weight, boll number, lint percentage, fiber quality, and the like. These IBD segments were genomic segments common to the seven elite parents, which could reflect the genetic origins and genomic control segments of the common excellent traits of the seven elite parents, and were of great significance for the selection and improvement of elite parents of cotton hybrids.

In the above IBDs intersecting with QTL loci, the fragment D02: 2204597-2360776 contained nine quantitative trait loci associated with boll weight, lint percentage, seed index and the like, and also intersected with a GWAS section for lint percentage (P=5.63E-07) (Fang et al., 2017). It was further clarified by real-time fluorescent quantitative PCR experiment and association analysis that GhWAKL3 had an important effect on lint percentage in cotton fiber. The variations of the locus SNP_D02_2254167 on GhWAKL3 had two allelic variants (A/G) in a population, and the statistical results of lint percentage in multiple environments showed that the allelotype GG was a favorable allelic variation.

Genomes extracted from different cotton varieties were amplified by using any one of primer pairs set forth in SEQ ID NOs. 1-14, and the amplified products were sequenced and aligned to determine the nucleic acid of a SNP marker and identify whether it was a favorable variant.

Example 6

1. Materials and Methods

Selection of Test Accessions and Design of Field Experiments

In this study, a total of 276 upland cotton accessions, including cotton varieties which had played an important role in different historical stages and representative cotton varieties from the National Cotton Germplasm Resource Mid-term Storage Library of the Cotton Research Institute of Chinese Academy of Agricultural Sciences as well as breeding basic materials accumulated by our research team in the long-term practice of breeding of high-yielding varieties, were mainly collected for subsequent association analysis.

These accessions could be classified into five groups according to geographical origin: varieties in Yellow River Region (YRR) of China, varieties in Yangtze River Region (YtRR) of China, accessions in Northwest Inland Watershed (NW) of China, varieties in Northern Special Early Maturing Region (NSEMR) of China, and varieties from other countries in the world. All the accessions were respectively planted in five locations in China from 2016 to 2017, namely, in Anyang, Henan Province (2016-2017), Jingzhou, Hubei Province (2016-2017), Jiujiang, Jiangxi Province (2016), Huanggang, Hubei province (2017), and Anqing, Anhui Province (2017), and were designated as 16AY, 16JZ, 16H, 17AY, 17JZ, 17HG, and 17AQ, respectively. All the field experiments were arranged in a completely randomized block design with two replications. In each environment, all the accessions were planted in a single row with a length of 6.0 meters and a width of 0.8 meters, and 20 to 25 plants were grown per row. Field management in each planting environment followed the local conventional methods.

2. Identification of Agronomic Traits and Statistical Analysis of Phenotypic Data During the boll opening and blooming period, 25 cotton bolls with normal boll opening were randomly harvested from the middle portions of ten plants per row for calculation of lint percentage. The lint percentage was calculated based on the following formula: lint percentage (LP for short) (%)=lint yield/seed-cotton yield. Basic descriptive statistical analysis, Pearson correlation analysis of lint percentage traits between different environments, and a two-way analysis of variance (Two-way ANOVA) were conducted on phenotypic data about lint percentage traits in multiple environments using R software package. In addition, the best linear unbiased prediction (BLUP) and broad-sense heritability were calculated for the lint percentage traits in all the environments using the lme4 software package in R language. The broad-sense heritability ($H^2$) of the lint percentage was calculated based on the formula $H^2=\sigma^2_G/(\sigma^2_G+\sigma^2_{GE}/n+\sigma^2_e/nr)$ where $\sigma^2_G$ was the genetic variance, $\sigma^2_{GE}$ E was the genotype-environment interaction (G×E) variance, $\sigma^2_e$ was the error variance, n represented the number of environments, and r represented the number of replications. Here, parameters such as $\sigma^2_G$, $\sigma^2_{GE}$ and $\sigma^2_e$ were estimated using the lmer function in the lme4 software package.

3. Analysis of LP Phenotypic Variation

In this study, 276 upland cotton accessions from different ecoregions were collected and constructed into natural populations for genome-wide association analysis. Phenotypes were examined in different environments, and phenotypic data exhibited abundant variations.

Figure 10:
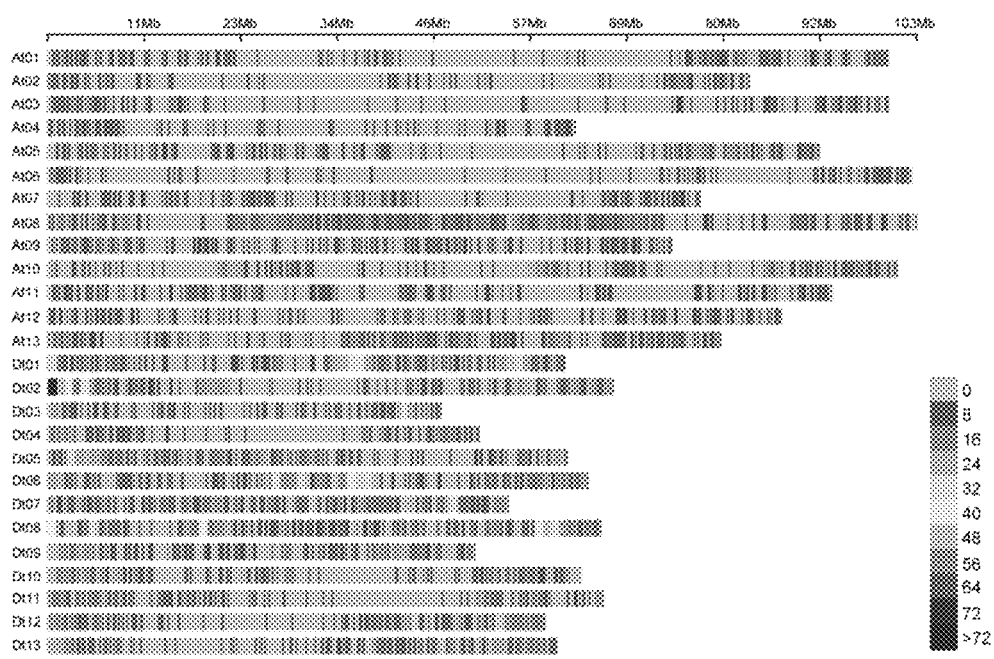
FIG. 10 is a diagram showing the distribution of SNPs on 26 chromosomes of upland cotton in Example 6 of the present disclosure.

In seven environments, LP was distributed between 10.49% and 49.62% with a mean value of 37.60%. The coefficient of variation ranged from 7.68% to 11.20% in different environments, and the mean value of lint percentage was 35.97% to 39.53% (Table 2). In addition, the absolute values of kurtosis and skewness of the traits in different environments were less than 1 or approximately 1. Thus, it could be seen that the lint percentage trait exhibited an approximately continuous normal distribution in all environments (FIG. 10).

In order to reduce the impact of the environment on the trait phenotype, the BLUP values of the lint percentage phenotypes in all environments were estimated. The BLUP value of the lint percentage trait ranged from 22.37% to 43.28%, with a mean value of 37.51%, and the coefficient of variation was 7.78%. The results of analysis of variance showed that genotype (G), environment (E), and the interaction between genotype and environment (G×E) all reached an extremely significant level (Table 3).

TABLE 3

Results of Analysis of Variance

| Feature | Variance | SS | MS | F | P value | $H^2$ (%) |
|---|---|---|---|---|---|---|
| LP | E | 36990 | 134.5 | 28.668 | <0.0001 | 90.7 |
|  | G | 5780 | 963.3 | 205.313 | <0.0001 |  |
|  | G × E | 13442 | 8.2 | 1.748 | <0.0001 |  |

Figure 11:
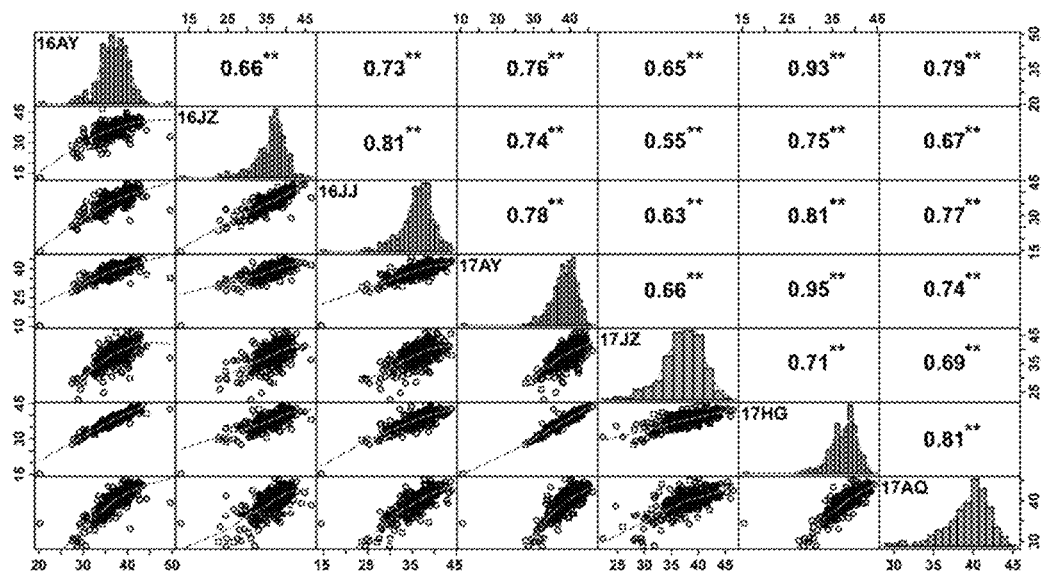
FIG. 11 is a diagram showing phenotypic performance of the lint percentage trait of 276 upland cotton accessions in multiple environments in Example 6 of the present disclosure.

In addition, the broad-sense heritability of LP was up to 90.7% (Table 3). Then, it was found by a correlation analysis of the lint percentage trait between different environments that there was a significant positive correlation relationship between lint percentage phenotypes in different environments (FIG. 11). In summary, the lint percentage trait was relatively stable and mainly controlled by genetic effects, and was thus suitable for association analysis.

Example 7

DNAs were extracted from young leaf tissues of each accession using a modified CTAB method. The accessions were genotyped using a CottonSNP63K array. Quality control of SNP genotyping results was performed using GenomeStudio v2011.1 analysis software. Then, the SNPs were further screened according to criteria such as call rate>85% and minor allele frequency (MAF)>0.05. Finally, the probe sequences of the SNPs were aligned with the upland cotton reference genome TM-1 (Gossypium hirsutum (AD1) Genome NAU-NBI Assembly v1.1 & Annotation v1.1) so as to obtain the physical positions of the SNPs.

The alignment results showed that 14,977 SNPs were aligned to the scaffold region where a chromosomal position was not determined, and 48,081 SNPs were aligned to chromosomes, and these SNPs aligned to chromosomes would be used for further analysis. Then, the SNPs were filtered according to the set filtering criteria, i.e., call rate>85% and MAF>0.05. Finally, 10,660 high-quality SNPs were obtained and used in subsequent association analysis.

TABLE 2

Basic Descriptive Statistics of Phenotypic Data on lint Percentage Trait

| Classification of Planting Locations | Minimum LP | Maximum LP | Mean Value | SD | CV (%) | Skewness | Kurtosis |
|---|---|---|---|---|---|---|---|
| 16AY | 20.30 | 49.62 | 36.85 | 3.35 | 9.09 | −0.625 | 2.446 |
| 16JZ | 12.89 | 46.51 | 36.24 | 4.06 | 11.20 | −1.442 | 4.496 |
| 16JJ | 14.52 | 43.96 | 35.97 | 3.79 | 10.55 | −1.213 | 3.782 |
| 17AY | 10.49 | 46.20 | 38.86 | 3.71 | 9.54 | −2.053 | 11.821 |
| 17JZ | 22.33 | 46.51 | 37.90 | 3.93 | 10.37 | −0.708 | 0.969 |
| 17HG | 15.39 | 44.29 | 37.86 | 3.31 | 8.76 | −1.614 | 7.255 |
| 17AQ | 28.83 | 45.26 | 39.53 | 3.04 | 7.68 | −1.085 | 1.480 |
| BLUP | 22.37 | 43.28 | 37.51 | 2.92 | 7.78 | −1.200 | 2.760 |

These high-quality SNP markers were unevenly distributed across the 26 chromosomes, with more SNPs found on the Dt subgenome (6480) than on the At subgenome (4180). The distribution density of the SNP markers on the 26 chromosomes ranged from 86.43 kb/SNP (Dt07) to 731.71 kb/SNP (At06), with an average marker density of 237.32 kb/SNP. In addition, the polymorphic information content (PIC) values varied from 0.200 (Dt06) to 0.294 (At13) among the 26 chromosomes, with a mean value of 0.250.

The mean value of gene diversity of all chromosomes was 0.31 and ranged from 0.24 (Dt06) to 0.37 (At01, At05 and At13) (Table 4).

TABLE 4

Statistical Table of Information such as SNPs, PIC, and Gene Diversity on the 26 Chromosomes of Upland Cotton

| Chr | Chr Length (kb) | SNPs | SNP Density (kb/SNP) | PIC | Gene Diversity |
|---|---|---|---|---|---|
| At01 | 99884.700 | 351 | 284.57 | 0.293 | 0.37 |
| At02 | 83447.906 | 166 | 502.70 | 0.259 | 0.32 |
| At03 | 100263.045 | 225 | 445.61 | 0.280 | 0.35 |
| At04 | 62913.772 | 132 | 476.62 | 0.272 | 0.34 |
| At05 | 92047.023 | 324 | 284.10 | 0.292 | 0.37 |
| At06 | 103170.444 | 141 | 731.71 | 0.239 | 0.29 |
| At07 | 78251.018 | 275 | 284.55 | 0.250 | 0.31 |
| At08 | 103626.341 | 846 | 122.49 | 0.240 | 0.29 |
| At09 | 74999.931 | 303 | 247.52 | 0.271 | 0.34 |
| At10 | 100866.604 | 405 | 249.05 | 0.222 | 0.26 |
| At11 | 93316.192 | 294 | 317.40 | 0.213 | 0.26 |
| At12 | 87484.866 | 245 | 357.08 | 0.261 | 0.32 |
| At13 | 79961.121 | 473 | 169.05 | 0.294 | 0.37 |
| Dt01 | 61456.009 | 638 | 96.33 | 0.242 | 0.30 |
| Dt02 | 67284.553 | 694 | 96.95 | 0.289 | 0.36 |
| Dt03 | 46690.656 | 235 | 198.68 | 0.209 | 0.25 |
| Dt04 | 51454.130 | 259 | 198.66 | 0.266 | 0.33 |
| Dt05 | 61933.047 | 495 | 125.12 | 0.260 | 0.32 |
| Dt06 | 64294.643 | 697 | 92.24 | 0.200 | 0.24 |
| Dt07 | 55312.611 | 640 | 86.43 | 0.246 | 0.30 |
| Dt08 | 65894.135 | 677 | 97.33 | 0.273 | 0.34 |
| Dt09 | 50995.436 | 458 | 111.34 | 0.232 | 0.28 |
| Dt10 | 63374.666 | 462 | 137.17 | 0.264 | 0.33 |
| Dt11 | 66087.774 | 379 | 174.37 | 0.235 | 0.29 |
| Dt12 | 59109.837 | 436 | 135.57 | 0.252 | 0.31 |
| Dt13 | 60534.298 | 410 | 147.64 | 0.234 | 0.29 |

Example 8

A population structure of 276 upland cotton accessions was analyzed based on a Bayesian model in STRUCTURE 2.3.4 software. The number of populations (K) was set to 1-10, wherein a length of burn-in period was set to be 100,000, Marko chain monte carlo (MCMC) was set to be 100,000, and five independent runs were performed for each K value. Then, the optimal number of subpopulations of the population was estimated based on the LnP(K) and ΔK values with reference to the Evanno method or the like. A population structural matrix (Q matrix) was obtained by integrating the results of the five runs for the optimal K value using CLUMPP software. In addition, principal component analysis (PCA) and kinship analysis were performed using the GAPIT software package. PowerMarker v3.25 software was used to calculate the polymorphic information content (PIC), gene diversity, and Nei's genetic distances. Then, a phylogenetic tree was constructed according to Nei genetic distances using MEGA 6.0 software. Finally, a linkage disequilibrium coefficient $r^2$ between different loci was calculated using PLINK software, with the parameter being set as—1d-window-r2 0—1d-window 99999—1d-window-kb 1000.

Phenotypic data and genotypic data on lint percentage in multiple environments are integrated for genome-wide association analysis based on the mixed linear model (MLM) method in the GAPIT software package in R language and using the population structure matrix (constituted by the first three principal components) and the kinship matrix (K) as covariates. The significance threshold (P) in the association result was calculated according to the number of markers (P=1/n, n was the total number of SNPs used). LD blocks were analyzed and drawn using Haploview 4.2 software. Manhattan plots were drawn by the qqman software package in R language.

In the genome-wide association analysis, the genetic structure of the association population might influence the reliability of the results. Therefore, it was necessary to evaluate the population structure of the association population. Here, the population structure was analyzed using three different methods based on 10,660 genotyped results, as specifically shown in FIG. 12, where (a) was a graph showing the change in LnP(K) when K=1 to 10; (b) was a graph showing the relationship between ΔK and K values; (c) showed the population structure of the natural population when K=2, (d) showed the principle component analysis; and (e) showed a NJ cluster tree based on Nei's genetic distances.

Figure 12:
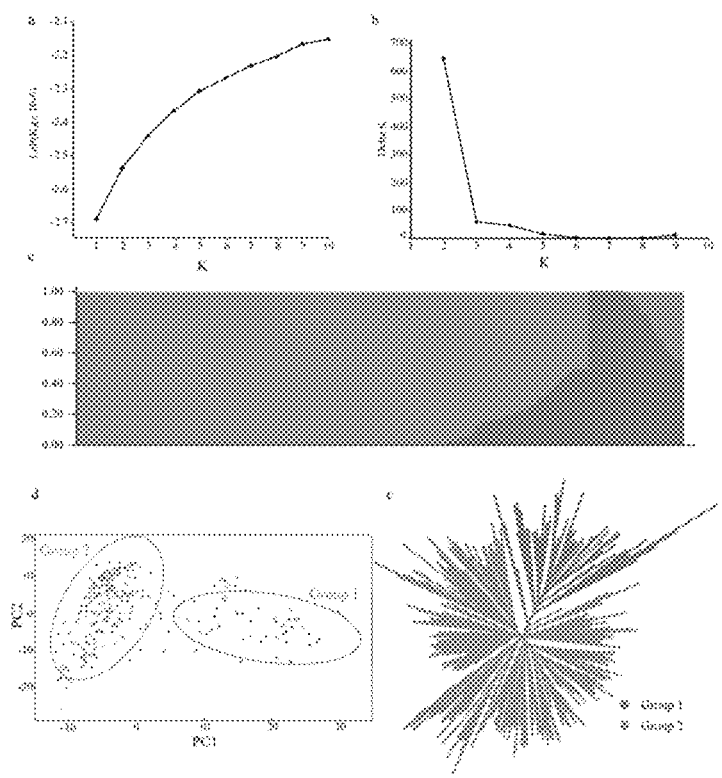
FIG. 12 is a diagram showing the population structure of a natural population in Example 8 of the present disclosure.
Figure 13:
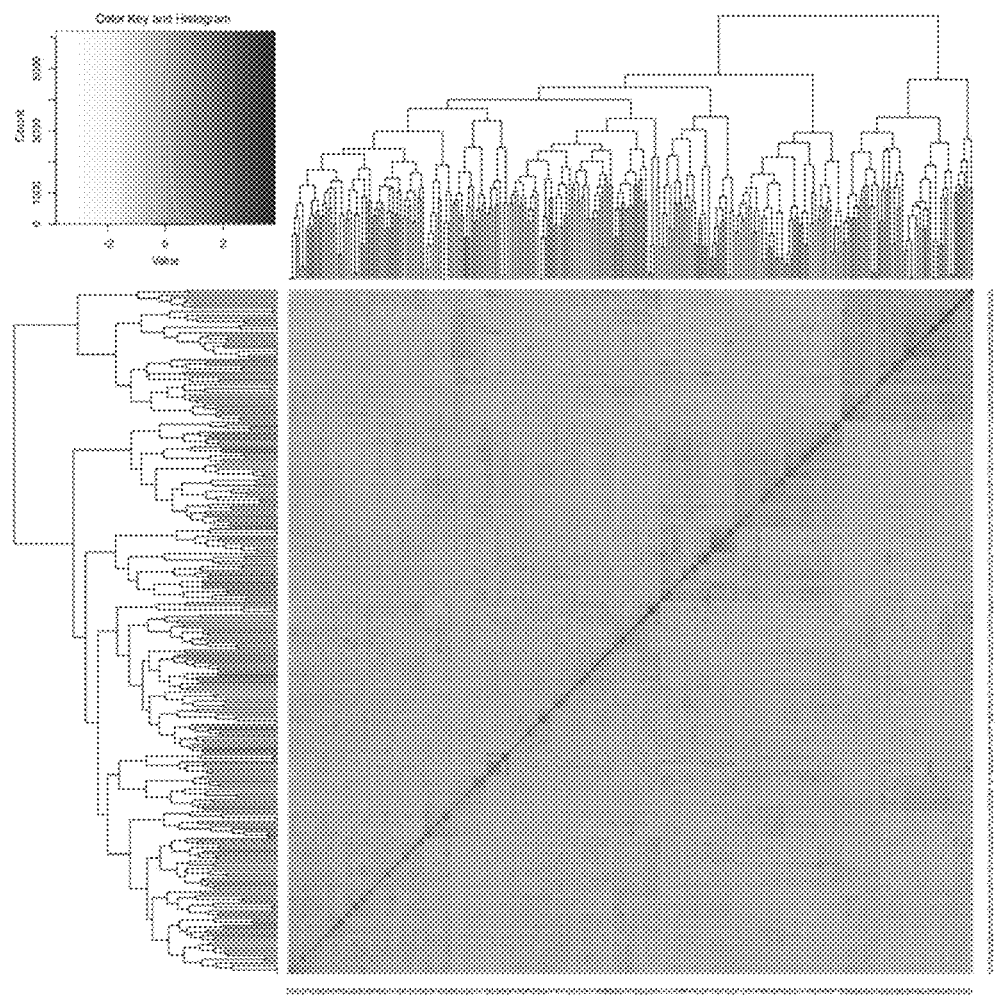
FIG. 13 is a heat map showing kinships between 276 upland cotton accessions in Example 8 of the present disclosure.

First, the results of analysis of the genetic structure of the population by the STRUCTURE software showed that the LnP(K) value increased continuously as K increased from 1 to 10 (FIG. 12a). When K=2, ΔK reached the maximum value (FIG. 12b). This indicated that there were two subpopulations in this population (FIG. 12c). The principal component analysis had a similar result to the population structure analysis. Here, some accessions were admixed between the two subpopulations (FIG. 12). The results of the neighbor-joining phylogenetic tree showed that the association population could be divided into two cluster groups (FIG. 12e). Similarly, the results of the clustering plot of the kinship analysis also coincided with the above results (FIG. 13). In summary, the natural population in this study could be divided into two subpopulations.

Figure 14:
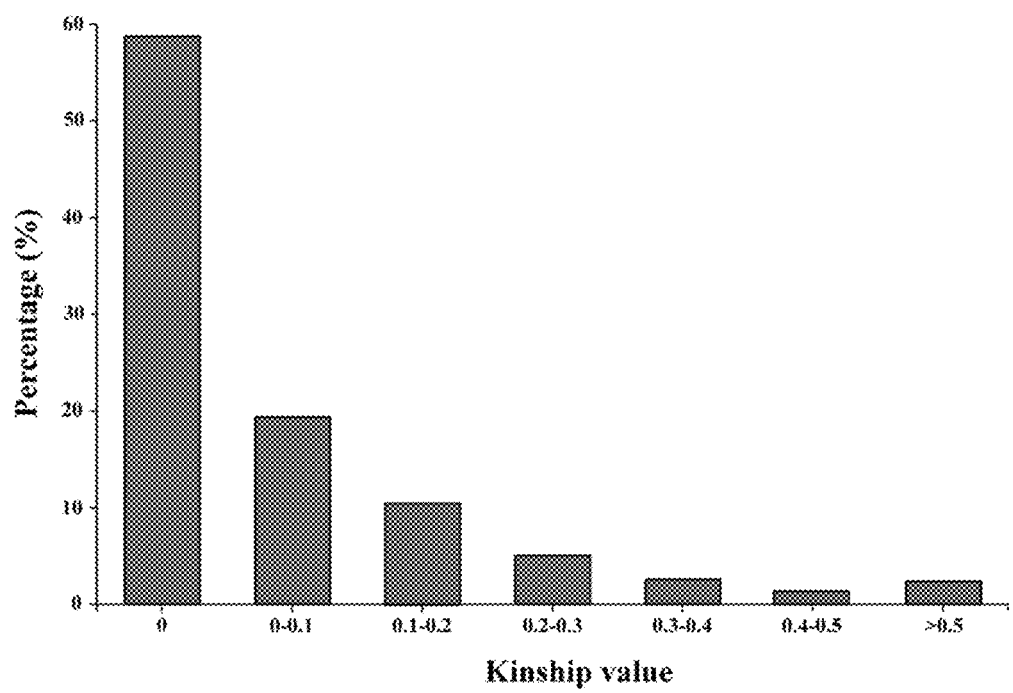
FIG. 14 is a diagram showing the distribution of kinship coefficients of the natural population in Example 8 of the present disclosure.
Figure 15:
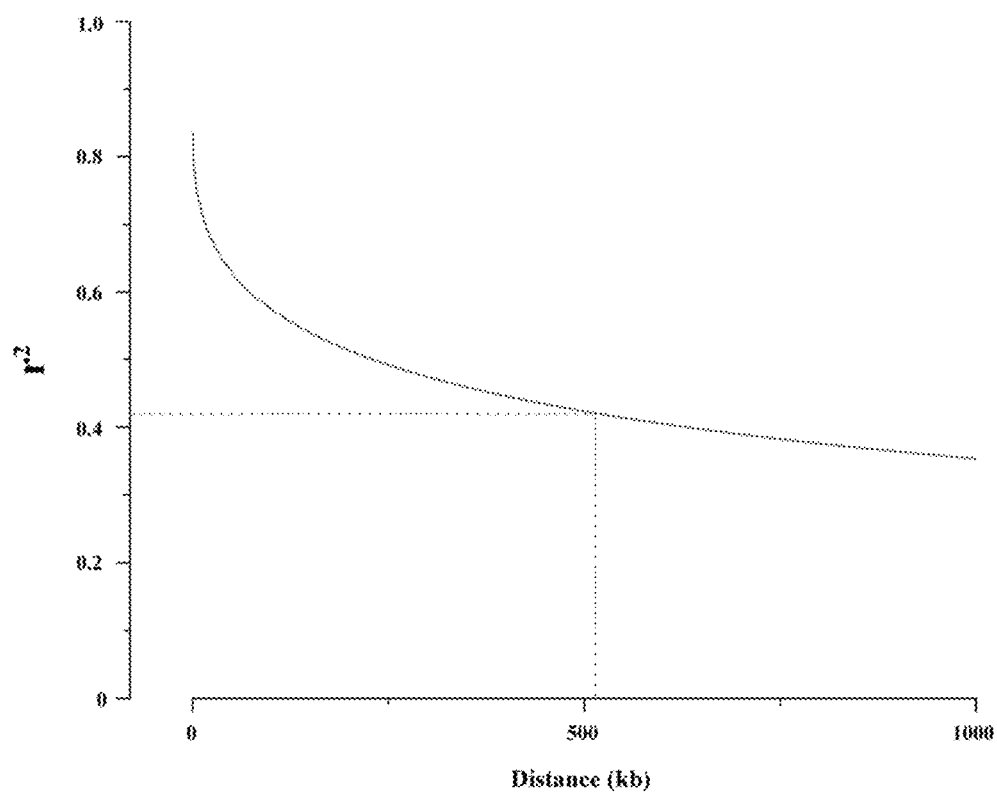
FIG. 15 is a diagram showing the genome-wide LD decay of the natural population in Example 8 of the present disclosure.

The kinship between individuals within a population was another factor affecting the mapping accuracy of association analysis. In this study, the kinship coefficients between most (about 88.71%) of the accessions were less than 0.2. Among them, 58.74% of the accessions had a kinship coefficient of 0, and only 2.37% of the accessions had a kinship coefficient greater than 0.5 (FIG. 14). These results indicated that there was weak kinship between the individuals of the natural population selected in this study. We found by the statistics of the linkage disequilibrium parameter $r^2$ between SNP loci that the LD decay distance of this population was about 530 kb (FIG. 15).

It could be seen from the above results that the natural population selected by us did not have a complicated population structure, there was weak kinship between individuals in the population, and the population had a moderate LD decay distance. Therefore, this population was suitable for genome-wide association analysis.

Example 9

1. Genome-wide Association Analysis of Lint Percentage Trait

In this study, in order to reduce the false positives of the association results, the mixed linear model (MLM) method was used, and the population structure (PCs) and the kinship (K matrix) of the principle component analysis were used as covariates for association analysis. The identified high-quality SNP data and field phenotypic data (including phenotypic data in individual environments and BLUP values) were integrated for association analysis to explore and analyze genetic loci or candidate genes for regulating the lint percentage trait.

Figure 16:
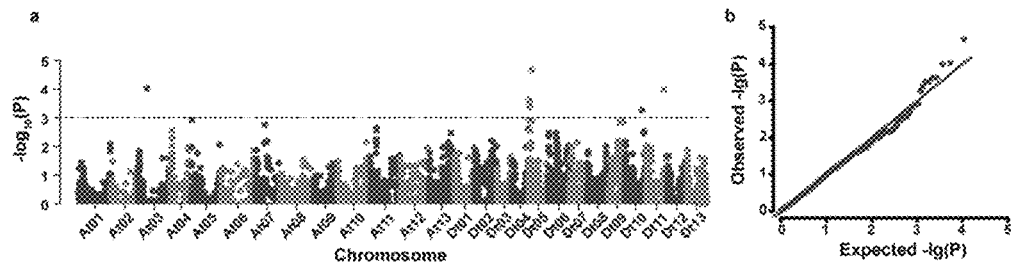
FIG. 16 is a diagram showing genome-wide association analysis of a BLUP value of the lint percentage trait in Example 9 of the present disclosure.

The significance threshold was adjusted to $P=1.0 \times 10^{-3}$ according to the results of association of the lint percentage traits in different environments. Finally, a total of 23 SNPs randomly distributed on 13 chromosomes were identified as significantly associated with the LP (FIG. 16a). Among them, seven were located on chromosome Dt05, four on chromosome Dt10, and two on chromosome Dt13, and the remaining ten SNPs were located on the other ten different chromosomes, i.e., At01, At03, At05, At07, At10, Dt01, Dt02, Dt04, Dt09, and Dt11. The phenotypic variation explained by these SNPs ranged from 4.20% to 10.23%, with an average of 5.68%. In addition, eleven SNPs were simultaneously detected in at least two environments. Among them, four SNPs (i56741Gb, i61131Gt, i08888Gh, and i00252Gh) located on chromosomes At03 and Dt05 were simultaneously detected in five environments. The SNP locus i56741Gb located on chromosome At03 had the highest $-\log_{10}$ (P) value of 5.10 and explained the largest amount of phenotypic variation (10.23%). The SNP locus i00252Gb located on chromosome Dt05 had the highest $-\log_{10}$ (P) value (5.06) and had the largest phenotypic contribution rate (8.05%) to the trait on chromosome Dt05. In FIG. 16, (a) was a Manhattan plot of the BLUP value association analysis. (b) was a Q-Q plot of BLUP value association analysis.

In consideration of the linkage disequilibrium decay distance of the association population in this study and with reference to the previous definition of QTL, we regarded the 200 kb upstream and downstream regions of a SNP significantly associated with the LP as a QTL and considered adjacent QTLs with overlapping physical sections to be the same QTL. Based on this rule, 15 QTLs were detected, and these QTLs were distributed across different chromosomes. These QTLs contained only one significant SNP locus, except for the four QTLs, qLP-Dt05-1 (containing five significant SNP loci), qLP-Dt05-2 (containing two significant SNP loci), qLP-Dt10-2 (containing three significant SNP loci), and qLP-Dt13 (containing two significant SNP loci).

2. Co-Localization with the Reported QTLs

In order to verify the feasibility of the GWAS method and the reliability of the association results in this study, the QTLs detected herein were compared with QTLs for LP trait previously reported using the linkage analysis or association analysis method.

First, the reported QTL and GWAS loci for LP trait were collected from the CottonQTLdb database. Then, primer sequences of SSR markers were downloaded from the Cottongen database. Finally, the primer sequences were aligned with the reference genome using e-PCR program to determine the physical positions of the SSR markers. The SNP loci and the SSR markers were integrated into one physical map and then compared.

It was identified by this method that nine QTLs, which were respectively distributed on different chromosomes, At03, At05, At10, Dt02, Dt04, Dt05, Dt09, Dt10 and Dt11, were co-localized with 11 previously reported QTLs. Among them, six of the QTLs shared overlapping regions with the reported QTLs (qLp-A-1, qLP-Chr10-1, qLP-Chr14-1, qLP-Chr21-2, TMB0206, and MGHES46), and the remaining QTLs were adjacent to qGhLP-c5, JESPR220, NAU3269, qLP-19 or qLP-D10_16, respectively. These results verified the reliability of our experiment methods and association results.

Example 10

1. Transcriptome Sequencing Data and Fluorescent Quantitative PCR Analysis

Transcriptome sequencing data from cotton tissues (root, stem, leaf, ovule and fiber developmental stages) of the upland cotton reference genome (TM-1) were downloaded from the public database NCBI. Sequence alignment and gene expression analysis of the transcriptome sequencing data were performed using TopHat and Cufflinks software. Finally, the gene expression amounts were represented by FPKM (Fragments per kb Million fragments) values. RNAs was extracted from cotton ovules at different developmental stages (0, 10, 20, and 30 DPA) and fibers at different developmental stages (10, 20, and 30 DPA) using Trizol kit, and the concentration of RNAs was detected using Nanodrop2000 ultramicro-volume spectrophotometer, and then the RNAs were reversely transcribed using TaKaRa reverse transcription kit. The experiment was performed on a LightCycler480 fluorescent quantitative PCR machine based on a dye method (SYBR). Gene GhHistone3 was selected and used in the experiment as an internal reference gene, and the results of the fluorescent quantitative PCR experiment were analyzed using the $2^{-\Delta Ct}$ method. Gene-specific primers were shown in Table 5.

TABLE 5

Primer Information for Fluorescent Quantification

| Gene name | Forward Primer (5'-3') | Reverse Primer (5'-3') |
|---|---|---|
| Gh_D05G1124 | GGATTCTGAAAGCTGGTGGT (SEQ ID NO. 24) | CAATTTGCCTTT CAGCAGGT (SEQ ID NO. 25) |
| Gh_D05G0313 | TGCCTTTTGGAAAGCAAATC (SEQ ID NO. 26) | GCAACTCTCGTT CCTTGCTC (SEQ ID NO. 27) |
| GhHis3 | TCAAGACTGATTTGCGTTT CCA (SEQ ID NO. 28) | GCGCAAAGGTTG GTGTCTTC (SEQ ID NO. 29) |

2. Identification of Candidate Genes

In this study, a total of 434 candidate genes were identified. The results of analysis of RNA-seq data from different tissues of the upland cotton reference genome TM-1 showed that 263 of the genes were predominantly expressed in different tissues and organs. Some of these genes, such as GhUPL7, GhTUB5, and GhCK1, had been determined to be involved in cotton fiber development. This illustrated the reliability of the method for identifying candidate genes in the present disclosure.

In order to further determine SNP loci or genes associated with the LP trait, we focused on the SNP loci continuously identified in multiple environments and having the highest significance. The SNP locus i00252Gh located on chromosome Dt05 was not only simultaneously identified in five environments, but also exhibited the lowest P value and explained the largest phenotypic variation. Therefore, i00252Gh was used as a subject for further study.

Figure 17:
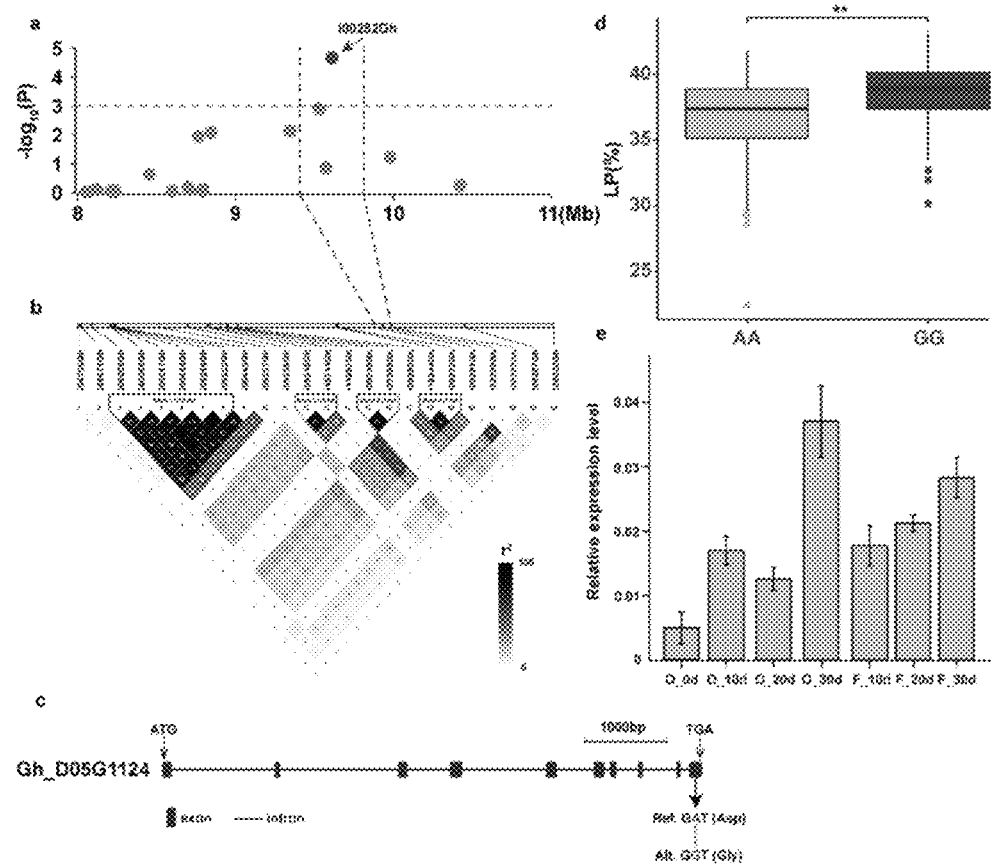
FIG. 17 is a diagram showing correlation analysis of candidate gene Gh_D05G1124 in Example 10 of the present disclosure.

In this study, the candidate regions were identified using 200 kb flanking the significant SNP locus. On this basis, a candidate section of 9.41 to 9.81 Mb was identified on Dt05 (FIGS. 17a and b). Here, FIG. 17a was a local Manhattan plot for a candidate region on chromosome Dt05; and FIG. 17b showed LD block analysis of the candidate region.

The LD block analysis indicated that the SNP locus i00252Gh subjected to focused study did not fall into any block region (FIG. 17b). But it was found that the locus i00252Gh was located in the 10th exon region of gene Gh_D05G1124, and i00252Gh was a non-synonymous mutant SNP. Specifically, i00252Gh was located at base 9611840 of chromosome Dt05. Mutation in the base resulted in a change in an amino acid, i.e., conversion from aspartic acid to glycine (FIG. 17c). FIG. 17c showed the structure of the candidate gene and a non-synonymous mutant locus thereof.

The gene was homologous to a gene encoding a protein phosphatase 2C family protein in Arabidopsis. In addition, a study was made on the effects of different alleles at the same locus on the LP trait. The study found that allele G had a positive effect on the phenotype of LP, that is to say, accessions carrying the G allele had significantly higher LP than those with the A allele (FIG. 17d). FIG. 17d showed differential performance of the lint percentage trait of accessions with different alleles.

Further, RNA-seq data from different tissues of upland cotton TM-1 showed that Gh_D05G1124 was predominantly expressed during ovule and fiber development (FIG. 17e). FIG. 17e showed expression levels of the candidate gene during ovule and fiber development. The qRT-PCR analysis indicated that the expression amount of this gene gradually increased during ovule and fiber development, with peak levels observed at 30 DPA in ovules and at 30 DPA in fibers. These results suggested that the gene Gh_D05G1124 participated in the development process of ovules and fibers of upland cotton and might be one of the candidate genes for regulating the lint percentage trait in upland cotton.

Figure 18:
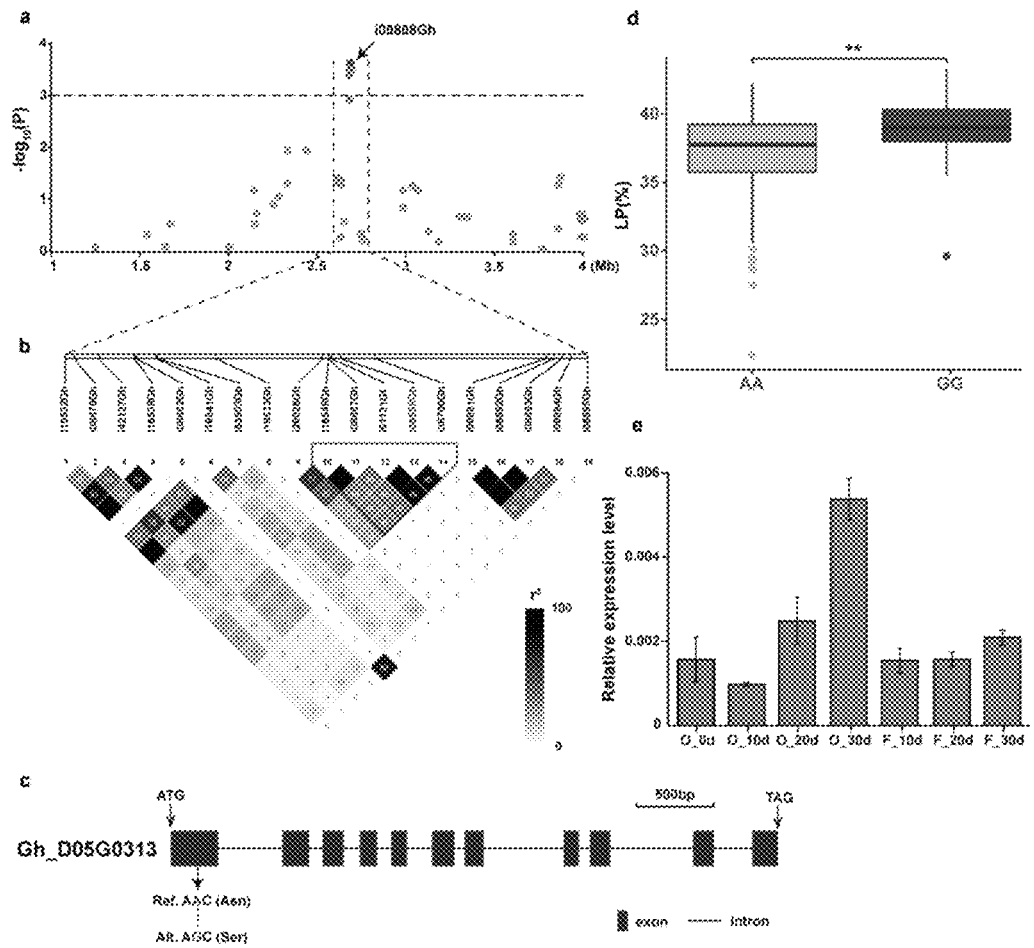
FIG. 18 is a diagram showing correlation analysis of candidate gene Gh_D05G0313 in Example 10 of the present disclosure.

Previous studies had shown that a polymorphism marker located in a gene region and resulting in a change in amino acid was most likely to be a functional locus associated with the target trait. On this basis, we found a non-synonymous SNP locus i08888Gh, which was located in an exon region of gene Gh_D05G0313, and caused a change in amino acid from aspartic acid to serine (FIGS. 18a-c). Specifically, i08888Gh was located at base 2687718 of the chromosome Dt05. FIG. 18a was a local Manhattan plot for a candidate region on chromosome Dt05; FIG. 18b showed LD block analysis of the candidate region; and FIG. 18c showed the structure of the candidate gene and a non-synonymous mutant locus thereof.

Furthermore, the LPs of the accessions in this study could be divided into two groups according to the allelotypes A and G of the locus. Accessions carrying the G allele had significantly higher LP than those carrying the A allele (FIG. 18d). FIG. 18d showed differential performance of the lint percentage trait of accessions with different alleles.

Furthermore, the qRT-PCR analysis indicated that Gh_D05G0313 was highly expressed in ovules at 30 DPA (FIG. 18e). FIG. 18e showed expression levels of the candidate gene during ovule and fiber development.

The homologous gene of Gh_D05G0313 in Arabidopsis was AtLUT2, which played an important role in photosynthesis of plants. Since photosynthesis was also required in the development of ovules and fibers of cotton, we inferred that this gene was another candidate gene for regulating the lint percentage.

Cotton fiber was formed by a highly elongated cell of the ovule epidermis, which was closely related to the processes such as protrusion of ovule epidermal fiber cells, fiber elongation, and secondary wall thickening. It was reported in previous studies that genes for regulating LP might be highly expressed during fiber development. So far, several genes associated with LP, such as Gh_A02G1268, Gh_D08G2376, AIL6 and EIL, Gh_D03G1064 and Gh_D12G2354, and Gh_D02G0025, had been identified by researchers via the GWAS method using different association populations. In this study, 434 genes were contained in the sections of identified 15 QTLs, and 263 of the genes were predominantly expressed in different tissues and organs. The present disclosure emphatically focused on the two genes, Gh_D05G1124 and Gh_D05G0313, because significant SNPs were located in their exon regions and resulted in changes in amino acids. Moreover, RNA-seq and qRT-PCR analysis revealed that both of the genes were highly expressed in ovules at 30 DPA. In addition, their homologous gene in Arabidopsis were respectively PP2C and AtLUT2, which were involved in protein phosphorylation and photosynthesis, respectively. Since the two processes were related to fiber development, the two genes, Gh_D05G1124 and Gh_D05G0313 were inferred as candidate genes for regulating LP.

3. Analysis of Elite Allelic Variation Loci

Elite allelic variations were valuable resources for crop breeding, and the accumulation of elite allelic variation loci was an efficient way to improve target traits in crop plants. The utilization of elite allelic variation loci had been reported in multiple crop plants. For example, some elite allelic variation loci were identified in wheat by GWAS, and it was also found that pyramiding of nine superior alleles contributed to an increased thousand-kernel weight in the wheat cultivar, Pindong34 in multiple environments, thus it was proposed that proper pyramiding of superior alleles was beneficial to improve yield trait in wheat. Similarly, in rapeseed, the researchers found that the aggregation of superior alleles significantly associated with earliness could result in earlier flowering or maturity.

Figure 19:
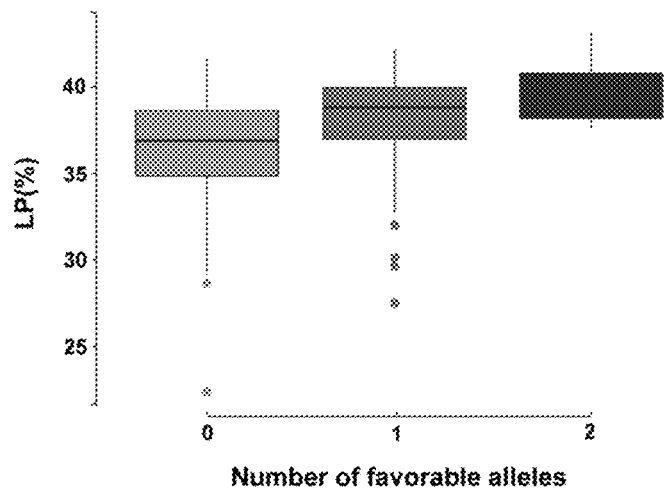
FIG. 19 is a diagram showing pyramiding effects of favorable allelic variations in Example 10 of the present disclosure.

Similar reports were also found in cotton. Li et al. selected three favorable SNP alleles to identify the effects of allelic variation on verticillium wilt resistance in upland cotton, and it was found that the disease resistance of accessions could be increased by pyramiding favorable SNP alleles. Correspondingly, it was found in the present study that two SNP loci significantly associated with LP, i00252Gh and i08888Gh, had a positive effect on LP phenotypic variation, that is to say, accessions carrying G allele at the loci i00252Gh and i08888Gh had higher LPs than those carrying the A allele. Moreover, it was found that the phenotypic value of LP increased continuously with the increased number of favorable alleles (FIG. 19). In other words, in FIG. 19, 0 represents accessions having no favorable allelic variation at the two loci i00252Gh and i08888Gh according to the present disclosure, 1 represents accessions having favorable allelic variations at any one of the two loci i00252Gh and i08888Gh according to the present disclosure, and 2 represents accessions having favorable allelic variations at both of the two loci i00252Gh and i08888Gh according to the present disclosure. Therefore, we can aggregate these elite allelic loci together by molecular marker-assisted so as to facilitate the improvement of the lint percentage trait in cotton breeding. Out of the 276 upland cotton accessions, however, only 16 varieties contain two favorable alleles. These elite allelic variation loci are not presently well utilized, and the future application of these favorable allelic variations thus has great potential in cotton breeding.

To sum up, in the present disclosure, 276 upland cotton accessions were used as materials and planted in multiple environments. A CottonSNP63K gene array was used for genotyping, and a total of 10,660 high-quality SNPs were obtained and used for genetic structure analysis and GWAS. A total of 23 SNPs and 15 corresponding QTLs were found by the GWAS analysis to be significantly associated with LP. In addition, Gh_D05G0313 and Gh_D05G1124 were determined by qRT-PCR analysis as candidate genes for regulating the LP trait. Furthermore, it was also found that the performance of the LP trait was positively correlated with the aggregation of favorable SNP alleles. Therefore, the pyramiding of these superior alleles may be beneficial to trait improvement in cotton breeding programs. In summary, the above findings enhance the understanding of the genetic basis of the LP trait in cotton and contribute to the exploration of the molecular mechanism of the lint percentage trait.

Although the present disclosure has been illustrated and described with specific examples, it will be appreciated that many other changes and modifications may be made without departing from the spirit and scope of the present disclosure. Accordingly, it is intended that all these changes and modifications falling within the scope of the present disclosure are encompassed by the appended claims

INDUSTRIAL APPLICABILITY (1) A SNP marker significantly associated with lint percentage in cotton is found for the first time in the present disclosure, which can be applied to germplasm identification, breeding or genetic diversity analysis, and provides a good basis for the study of cotton traits.

(2) Accessions with high lint percentage are selected by selecting a favorable allelic variation (GG genotype) at the marker locus, whereby the efficiency and accuracy of the selection are greatly increased, and the number of years required for breeding of accessions with high lint percentage is significantly shortened.

(3) The present disclosure provides genes significantly associated with lint percentage in cotton, which are obtained by analyzing a large amount of biological information using molecular biological means and traits, and which provide a good basis for trait improvement in cotton breeding programs.

(4) The present disclosure provides a product for detecting the SNP marker to facilitate the detection of the SNP marker.

The invention claimed is:

1. A method for selecting a cotton plant, comprising steps of:
   extracting a genome from cotton plant to be analyzed;
   analyzing said genome for the presence of genes Gh_D05G1124 and Gh_D05G0313;
   analyzing the tenth exon region of the gene Gh_D05G1124 at base 6498 from a start codon of the gene;
   analyzing the first exon region of the gene Gh_D05G0313 at base 176 from a start codon of the gene; and
   selecting the cotton plant if base 6498 of gene Gh_D05G1124 and base 176 of gene Gh_D05G0313 is a GG genotype.

2. A cotton breeding method, comprising steps of:
extracting a genome from cotton to be detected;
analyzing the tenth exon region of the gene Gh_D05G1124 at base 6498 from a start codon of the gene and analyzing the first exon region of the gene Gh_D05G0313 at base 176 from a start codon of the gene;
selecting the cotton plant if base 6498 of gene Gh_D05G1124 and base 176 of gene Gh D05G0313 is a GG genotype; and
propagating said selected cotton plant using materials suitable for sexual propagation, vegetative propagation, or tissue culture of regenerable cells.

3. The method according to claim 1, further comprising propagating said selected cotton plant using materials suitable for sexual propagation, vegetative propagation, or tissue culture of regenerable cells, wherein materials suitable for sexual propagation are selected from pollen, ovaries, ovules, embryo sacs, and egg cells; materials suitable for vegetative propagation are selected from cuttings, roots, stems, cells, and protoplasts; and materials suitable for tissue culture of regenerable cells are selected from leaves, pollen, embryos, cotyledons, hypocotyls, meristematic cells, roots, root tips; anthers, flowers, seeds, and stems.

4. The method according to claim 1, wherein analyzing gene Gh_D05G1124 or gene Gh_D05G0313 comprises one or more of: an gel electrophoresis-based SNP detection method, a DNA sequencing method, a DNA array method, denaturing high-performance liquid chromatography, and mass spectometry.

5. The method according to claim 2, wherein materials suitable for sexual propagation are selected from pollen, ovaries, ovules, embryo sacs, and egg cells; materials suitable for vegetative propagation are selected from cuttings, roots, stems, cells, and protoplasts; and materials suitable for tissue culture of regenerable cells are selected from leaves, pollen, embryos, cotyledons, hypocotyls, meristematic cells, roots, root tips, anthers, flowers, seeds, and stems.

6. The method according to claim 2, wherein analyzing gene Gh_D05G1124 or gene Gh_D05G0313 comprises one or more of: a gel electrophoresis-based SNP detection method, a DNA sequencing method, a DNA array method, denaturing high-performance liquid chromatography, and mass spectrometry.

\* \* \* \* \*